United States Patent
Cole, Jr. et al.

(10) Patent No.: US 10,943,701 B2
(45) Date of Patent: *Mar. 9, 2021

(54) THREE-DIMENSIONAL MODELING OF PATIENT-SPECIFIC TUMORS USING A LATTICE OF ELASTIC-MATERIAL POINTS TO SIMULATE METABOLISM, BIOCHEMICAL REACTIONS, MECHANICAL FORCES, AND DRUG INTERACTIONS IN A PATIENT

(71) Applicant: SimBioSys, Inc., Champaign, IL (US)

(72) Inventors: John A. Cole, Jr., Champaign, IL (US); Joseph R. Peterson, Champaign, IL (US)

(73) Assignee: SIMBIOSYS, INC., Champaign, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/540,911

(22) Filed: Aug. 14, 2019

(65) Prior Publication Data

US 2020/0118690 A1    Apr. 16, 2020

Related U.S. Application Data

(60) Provisional application No. 62/482,882, filed on Dec. 20, 2018, provisional application No. 62/745,114, filed on Oct. 12, 2018.

(51) Int. Cl.
| | |
|---|---|
| *G16H 50/50* | (2018.01) |
| *A61B 5/055* | (2006.01) |
| *G16H 15/00* | (2018.01) |
| *G16H 30/40* | (2018.01) |
| *G06F 3/0481* | (2013.01) |

(52) U.S. Cl.
CPC ............ *G16H 50/50* (2018.01); *A61B 5/055* (2013.01); *G16H 15/00* (2018.01); *G16H 30/40* (2018.01); *A61B 2576/00* (2013.01); *G06F 3/04815* (2013.01)

(58) Field of Classification Search
None
See application file for complete search history.

(56) References Cited

U.S. PATENT DOCUMENTS

| | | |
|---|---|---|
| 2004/0101176 A1 | 5/2004 | Mendonca et al. |
| 2016/0103971 A1* | 4/2016 | Hillis ............... G06F 19/30 703/11 |
| 2016/0300010 A1 | 10/2016 | Ruppin et al. |
| 2019/0198177 A1 | 6/2019 | Thomas, Jr. et al. |

FOREIGN PATENT DOCUMENTS

| | | |
|---|---|---|
| WO | 2005036446 A2 | 4/2005 |
| WO | 2018037137 A1 | 3/2018 |

OTHER PUBLICATIONS

Elliott, Nelita T., and F. A. N. Yuan. "A review of three-dimensional in vitro tissue models for drug discovery and transport studies." Journal of pharmaceutical sciences 100.1 (2011): 59-74.*
Imparato, G., F. Urciuolo, and P. A. Netti. "In vitro three-dimensional models in cancer research: a review." International Materials Reviews 60.6 (2015): 297-311.*
International Search Report and Written Opinion issued in International Application No. PCT/US2019/055724 dated Feb. 5, 2020 in 12 pages.

* cited by examiner

*Primary Examiner* — G Steven Vanni
(74) *Attorney, Agent, or Firm* — Procopio, Cory, Hargreaves & Savitch LLP; Jonathan Cheng; Robert Ramos

(57) ABSTRACT

Three-dimensional modeling of patient-specific tumors. In an embodiment, patient-specific data, representing a tumor microenvironment and one or more metrics, are received. A patient-specific spatial model, representing the tumor microenvironment as a lattice comprising a plurality of elastic material points, is generated from the patient-specific data. Patient-specific drug interaction and metabolism models are also determined. The tumor microenvironment is then simulated, for one or more drug interventions, through a plurality of iterations in which each elastic material point is updated in each iteration based on computations of chemical diffusion, biochemical reactions, metabolism, drug interactions, growth and death, and mechanical forces. A report, comprising a three-dimensional representation of the patient-specific spatial model after one or more iterations, is generated for the drug intervention(s).

36 Claims, 7 Drawing Sheets

440

THREE-DIMENSIONAL MODELING OF PATIENT-SPECIFIC TUMORS USING A LATTICE OF ELASTIC-MATERIAL POINTS TO SIMULATE METABOLISM, BIOCHEMICAL REACTIONS, MECHANICAL FORCES, AND DRUG INTERACTIONS IN A PATIENT

CROSS-REFERENCE TO RELATED APPLICATIONS

This application claims priority to U.S. Provisional Application No. 62/782,882, filed on Dec. 20, 2018, and U.S. Provisional Patent Application No. 62/745,114, filed on Oct. 12, 2018, which are both hereby incorporated herein by reference as if set forth in full.

BACKGROUND

Field of the Invention

The embodiments described herein are generally directed to modeling tumors, and, more particularly, to generating a three-dimensional (3D) model of a patient-specific tumor and simulating the patient-specific tumor's behavior over time.

Description of the Related Art

The prediction of tumor characteristics and treatment responses, based on genomics or gene-expression profiling is an active area of research and development. For example, gene-expression data enables the prediction of the sensitivity of different types of cancer cells to different drugs. "A Landscape of Pharmacogenomic Interactions in Cancer," by Iorio et al., Cell, 166(3):740-754 (2016) ("Iorio et al."), which is hereby incorporated herein by reference as if set forth in full, demonstrated that, out of several types of biological data, gene-expression profiling with knowledge of the tissue of origin enabled the greatest predictiveness of a cancer cell line's drug sensitivity. Furthermore, the last two decades have seen a deluge of patent applications for methods of predicting chemotherapeutic responsiveness, based on gene-expression profiling and other histological markers. See, e.g., International Patent Pub. Nos. WO/2010/076322, published on Jul. 8, 2010, and WO/2006/084272, published on Aug. 10, 2006, and U.S. Patent Pub. No. 2009/0239223, published on Sep. 24, 2009, which are all hereby incorporated herein by reference as if set forth in full.

In addition, gene-expression data can be used to construct personalized metabolism models. Several methods for this have been described in "iMAT: an integrative metabolic analysis tool," by Zur et al., Bioinformatics, 26(24):3140-3142 (November 2010), "Functional integration of a metabolic network model and expression data without arbitrary thresholding," by Jensen et al., Bioinformatics, 27(4):541-547 (December 2010), "Interpreting expression data with metabolic flux models: predicting *Mycobacterium tuberculosis* mycolic acid production," by Colijn et al., PLoS Comput. Biol., 5(8):e1000489 (2009), "Probabilistic integrative modeling of genome-scale metabolic and regulatory networks in *Escherichia coli* and *Mycobacterium tuberculosis*," by Chandrasekaran et al., Proceedings of the National Academy of Sciences, 107(41):17845-17850 (Sep. 2010), and "GIM3E: condition-specific models of cellular metabolism developed from metabolomics and expression data," by Schmidt et al., Bioinformatics, 29(22):2900-2908 (August 2013), which are all hereby incorporated herein by reference as if set forth in full. Most of these methods follow a similar tack. Beginning with a comprehensive model that accounts for every known metabolic reaction carried out by human cells, individual reactions and sets of reactions are pruned based on the expression levels of the enzymes that catalyze them, as measured via RNA-sequencing or microarray experiments.

However, what is needed is a simulation that constructs or selects the metabolic and/or drug responses that best represent a patient's tumor and surrounding tissues to achieve greater levels of patient specificity and realism.

SUMMARY

Accordingly, systems, methods, and non-transitory computer-readable media are disclosed for generating a three-dimensional model of a patient-specific tumor and simulating the patient-specific tumor's behavior over time.

In an embodiment, a method is disclosed that comprises using at least one hardware processor to: receive patient data for a patient, wherein the patient data comprises magnetic resonance imaging (MRI) data of a tumor microenvironment within the patient and one or more metrics of the patient; generate a patient-specific spatial model, comprising a representation of the tumor microenvironment as a lattice, from the MRI data within the patient data, wherein the lattice comprises a plurality of elastic material points representing tissue within the tumor microenvironment; determine a patient-specific drug interaction model based on the one or more metrics within the patient data; determine a patient-specific metabolism model based on the one or more metrics within the patient data; for each of one or more drug interventions, simulate the tumor microenvironment by, for each of a plurality of iterations representing time intervals, for each of the plurality of elastic material points, computing chemical diffusion within the tissue represented by the elastic material point and updating one or more properties of the elastic material point based on the computation of chemical diffusion, computing one or more biochemical reactions within the tissue represented by the elastic material point and updating one or more properties of the elastic material point based on the computation of the one or more biochemical reactions, computing a metabolism of the tissue represented by the elastic material point using the patient-specific metabolism model and updating one or more properties of the elastic material point based on the computation of metabolism, computing one or more drug interactions with the tissue represented by the elastic material point using the patient-specific drug interaction model and updating one or more properties of the elastic material point based on the computation of the one or more drug interactions, computing one or both of growth and death of the tissue represented by the elastic material point and updating one or more properties of the elastic material point based on the computation of one or both of growth and death, and computing mechanical forces at the elastic material point and updating one or more properties of the elastic material point based on the computed mechanical forces; and generate a report for at least one of the one or more drug interventions, wherein the report comprises a graphical user interface that comprises a three-dimensional visual representation of the patient-specific spatial model after one or more of the plurality of iterations. Simulating the tumor microenvironment may further comprise, for two or more of the plurality of iterations, for each of the plurality of elastic material points: computing chemical advection within the tissue represented by the elastic material point and updating one or more properties of the elastic material point based on the computation of chemical advection; computing regulation within the tissue represented by the elastic material point and updating one or more properties of the elastic material point based on the computation of regulation; and computing an immune system response within the tissue represented by the elastic material point and updating one or more properties of the elastic material point based on the computation of the immune system response. Computing an immune system response within the tissue represented by the elastic material point may comprise modeling immune cells as discrete motile agents. Computing an immune system response within the tissue represented by the elastic material point may comprise modeling immune cells as a scalar field that describes immune cell density. Computing regulation within the tissue represented by the elastic material point and updating one or more properties of the elastic material point based on the computation of regulation may comprise: receiving a current concentration of each of one or more chemicals at the elastic material point; receiving a current density and one or more mechanical properties of each of one or more tissues at the elastic material point; and, for each of the one or more tissues at the elastic material point, determining a regulatory state, and updating a regulatory state stored for the tissue to the determined regulatory state. Each regulatory state may represent one of a plurality of regulatory states, wherein each of the plurality of regulatory states is associated with a different one of a plurality of metabolism models, and wherein computing a metabolism of the tissue represented by the elastic material point comprises using the metabolism model associated with the regulatory state stored for the tissue. The regulatory state of each of the one or more tissues may be represented as a set of values that collectively describe a fraction of the tissue that is in each possible regulatory state. Computing chemical advection within the tissue represented by the elastic material point and updating one or more properties of the elastic material point based on the computation of chemical advection may comprise, for each of one or more chemicals, updating a concentration of the chemical at the elastic material point (i, j, k) as:

$$\varphi(i, j, k) \leftarrow \varphi(i, j, k) - \{[\varphi(i+1, j, k) \cdot u_x(i+1, j, k) - \varphi(i-1, j, k) \cdot u_x(i-1, j, k)] - [\varphi(i, j+1, k) \cdot u_y(i, j+1, k) - \varphi(i, j-1, k) \cdot u_y(i, j-1, k)] - [\varphi(i, j, k+1) \cdot u_z(i, j, k+1) - \varphi(i, j, k-1) \cdot u_z(i, j, k-1)]\} \cdot \frac{\Delta t}{2\lambda};$$

wherein $\varphi$ is a concentration of the chemical at the elastic material point, $\lambda$ is a lattice spacing between elastic material points in the lattice, and $u_x(i, j, k)$, $u_y(i, j, k)$, and $u_z(i, j, k)$ are components of a vector-valued flow field u at the elastic material point. Each of the plurality of elastic material points may be associated with a plurality of properties, wherein the plurality of properties comprise one or more chemical properties and one or more tissue properties. The one or more chemical properties may comprise a chemical concentration for one or more chemicals. The one or more tissue properties may comprise a density of the tissue represented by the elastic material point. The one or more tissue properties may comprise a permeability of the tissue represented by the elastic material point. The one or more tissue properties may comprise a regulatory state of the tissue represented by the elastic material point. Computing chemical diffusion within the tissue represented by the elastic material point and updating one or more properties of the elastic material point based on the computation of chemical diffusion may comprise: receiving a current concentration, diffusion rate, and boundary value for each of one or more chemicals at the elastic material point; receiving a current density of each of one or more tissues at the elastic material point; computing a new concentration for each of the one or more chemicals and a new density of each of the one or more tissues, based on the current concentration, diffusion rate, and boundary value for the one or more chemicals and the current density of the one or more tissues; for each of the one or more chemicals, updating the concentration of the chemical at the elastic material point to the new concentration; and, for each of the one or more tissues, updating the density of the tissue at the elastic material point to the new density. The patient-specific spatial model may be a spring model, such that each of the plurality of material points in the lattice is connected to each adjacent material point by a spring representation comprising a length value and a stiffness value. Different tissue types may be represented at the plurality of material points by different stiffness values. Updating one or more properties of the elastic material point based on the computed mechanical forces may comprise updating one or both of the length value and stiffness value of the spring representation between the material point and each adjacent material point. Updating one or more properties of the elastic material point based on the computed mechanical forces may comprise, until the mechanical forces reach an equilibrium: updating the length value of the spring representation between the material point and each adjacent material point based on the mechanical forces; and re-computing the mechanical forces at the material point. Each of the plurality of elastic material points may be associated with a plurality of properties, and wherein, for each of the one or more drug interventions, simulating the tumor microenvironment further comprises, at one or more times during the simulation, re-gridding the spatial model, such that each of the plurality of material points maintains its plurality of properties but all of the spring representations between pairs of material points have equal length values. The method may further comprise using the at least one hardware processor to simulate the tumor microenvironment without any drug intervention. The patient-specific metabolism model may be selected from a plurality of available metabolism models based on the one or more metrics within the patient data. The patient-specific metabolism model may comprise a flux balance analysis (FBA) model. The tumor microenvironment may comprise a tumor and tissues surrounding the tumor. The graphical user interface may comprise: a plurality of three-dimensional visual representations of the patient-specific spatial model at each of two or more of the plurality of iterations; and one or more inputs for navigating between the plurality of three-dimensional visual representations in a chronological order represented by the two or more iterations. The lattice may comprise a cubic lattice. Computing chemical diffusion within the tissue represented by the elastic material point may comprise, for each of one or more chemicals, modeling a chemical reaction as:

$$\varphi_{ext}(x, t + \Delta t) = \varphi_{ext}(x, t) - k(x, t)\Delta t;$$

$$\varphi_f(x, t + \Delta t) = \varphi_f(x, t) - k(x, t)\Delta t; \text{ and}$$

-continued
$$k(x, t) = \rho(x, t) \frac{Ek_{cat}}{V_{cell}} \frac{\varphi_{ext}(x, t)}{k_m + \varphi_{ext}(x, t)};$$

wherein $\varphi_{ext}(x, t)$ is an instantaneous local concentration of an extracellular form of the chemical, $\varphi_j(x, t)$ is an instantaneous local concentration of an intracellular form of the chemical, $\Delta t$ is the time interval represented by each of the plurality of iterations, $k(x, t)$ represents instantaneous local uptake rate of the chemical in the tissue, $\rho(x, t)$ represents an instantaneous local cell volume fraction of the tissue, E represents a number of enzymatic transporters on a cell membrane of the tissue, $V_{cell}$ represents a volume of a cell of the tissue, $k_{cat}$ represents an enzyme turnover rate, and $k_m$ is a Michaelis constant for the chemical reaction. Computing the metabolism of the tissue represented by the elastic material point may comprise: based on one or more parameters, performing a lookup in a precomputed table of solutions derived from a flux balance analysis (FBA) model of chemical uptake; and, when a solution does not exist in the precomputed table for the one or more parameters, interpolating a solution from one or more solutions that do exist in the precomputed table. Computing one or more drug interactions with the tissue represented by the elastic material point may comprise computing drug-related kinetics at the elastic material point for each of one or more drugs modeled by the patient-specific drug interaction model. The patient-specific drug interaction model may comprise a model of kinetic binding and unbinding rates for at least one drug. The patient-specific drug interaction model may comprise a model of uptake and efflux of at least one drug by one or more tissue types. Computing chemical diffusion within the tissue represented by the elastic material point may comprise modeling chemical diffusion using a seven-point stencil finite difference, in which an extracellular concentration of a chemical $\varphi$ at elastic material point i is updated as:

$$\varphi_i(t + \Delta t) = \varphi_i(t) + \frac{\Delta t}{\lambda} \sum_j J_{\varphi j \to i}(t);$$

$$J_{\varphi j \to i}(t) = \frac{D_{\varphi j}(t) + D_{\varphi i}(t)}{2} \frac{\varphi_j(t) - \varphi_i(t)}{\lambda};$$

wherein $\lambda$ is a lattice spacing between elastic material points in the lattice, j indexes over six elastic material points that neighbor elastic material point i, $J_{\varphi j \to i}(t)$ represents a diffusive flux across a boundary separating elastic material points j and i, $D_{\varphi i}$ is a diffusion coefficient for the chemical in elastic material point i, and $D_{\varphi j}$ is a diffusion coefficient for the chemical in elastic material point j. Computing a metabolism of the tissue represented by the elastic material point and updating one or more properties of the elastic material point based on the computation of metabolism may comprise: receiving one or more properties of each of one or more chemicals at the elastic material point, wherein the one or more properties comprise a current concentration; modeling a metabolism of each of one or more tissues at the elastic material point; computing a new concentration for each of the one or more chemicals and a growth rate for each of the one or more tissues, based on the one or more properties of the one or more chemicals and the modeled metabolism of the one or more tissues; or each of the one or more chemicals, updating the concentration of the chemical at the elastic material point to the new concentration; and, for each of the one or more tissues, updating a growth rate for the tissue to the new growth rate. Computing one or more biochemical reactions within the tissue represented by the elastic material point and updating one or more properties of the elastic material point based on the computation of the one or more biochemical reactions may comprise: receiving one or more properties of each of one or more chemicals at the elastic material point; receiving a density and regulatory state for each of one or more tissues at the elastic material point; determining drug impacts using the patient-specific drug interaction model; and updating concentrations of the one or more chemicals at the elastic material point based on the one or more properties of the one or more chemicals, the density and regulatory state of the one or more tissues, and the drug impacts. Computing one or more drug interactions with the tissue represented by the elastic material point using the patient-specific drug interaction model and updating one or more properties of the elastic material point based on the computation of the one or more drug interactions may comprise: receiving one or more properties of each of one or more drugs at the elastic material point; receiving a current density and determining a behavior for each of one or more tissues at the elastic material point; determining drug impacts of the one or more drugs using the patient-specific drug interaction model; and updating densities of the one or more tissues at the elastic material point based on the one or more properties of the one or more drugs, the current density and behavior of the one or more tissues, and the drug impacts. The patient-specific drug interaction model may identify a rate at which one or more drugs interact with and kill one or more tissue types. The method may be embodied in executable software modules of a processor-based system, such as a server, and/or in executable instructions stored in a non-transitory computer-readable medium.

BRIEF DESCRIPTION OF THE DRAWINGS

The details of the present invention, both as to its structure and operation, may be gleaned in part by study of the accompanying drawings, in which like reference numerals refer to like parts, and in which.

DETAILED DESCRIPTION

In an embodiment, systems, methods, and non-transitory computer-readable media are disclosed for generating a three-dimensional model of a patient-specific tumor and simulating the patient-specific tumor's behavior over time. After reading this description, it will become apparent to one skilled in the art how to implement the invention in various alternative embodiments and alternative applications. However, although various embodiments of the present invention will be described herein, it is understood that these embodiments are presented by way of example and illustration only, and not limitation. As such, this detailed description of various embodiments should not be construed to limit the scope or breadth of the present invention as set forth in the appended claims.

1. System Overview 1.1. Infrastructure

Figure 1A:
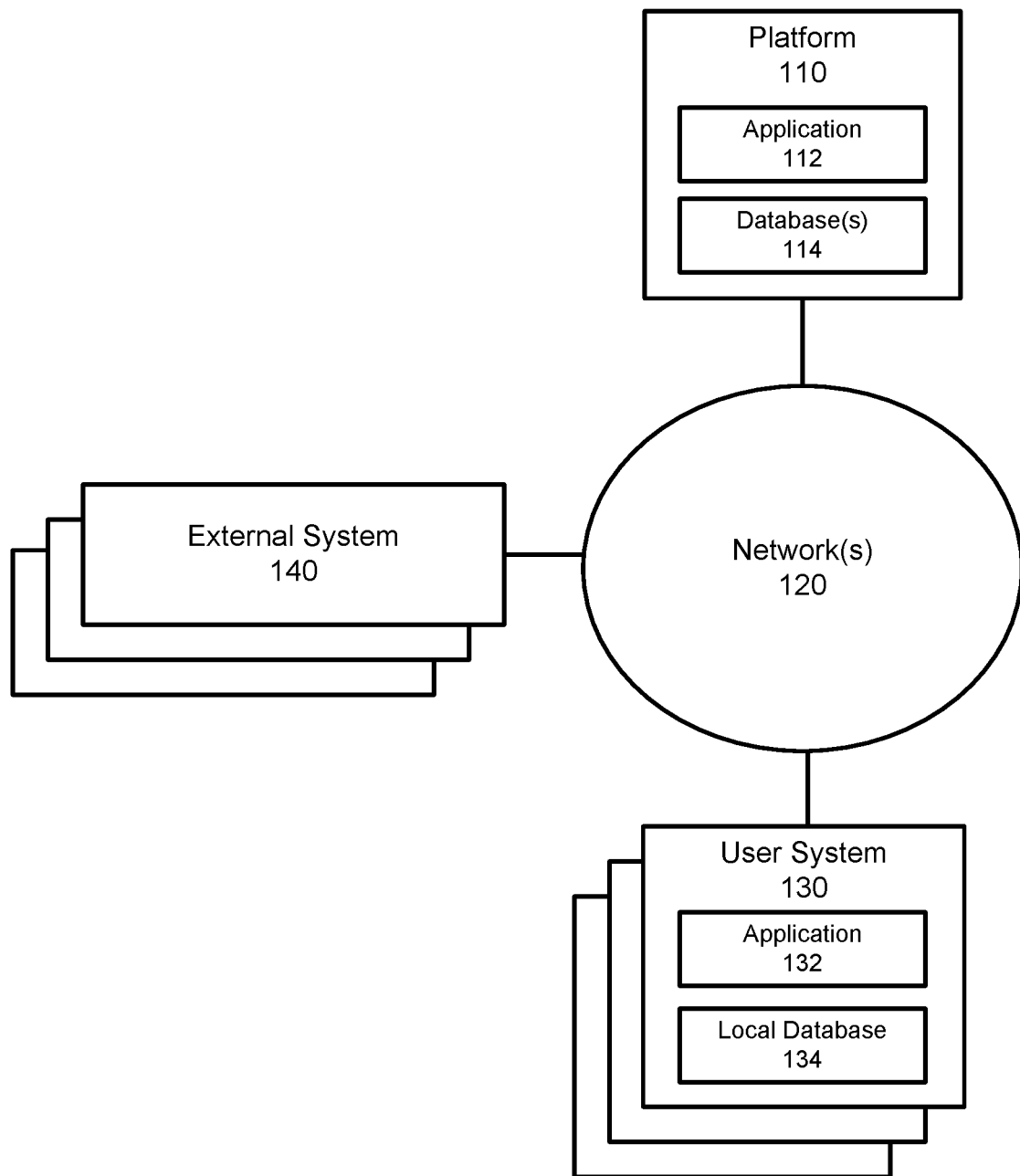
FIGS. 1A and 1B are block diagrams that illustrate example infrastructures, in which one or more of the processes described herein, may be implemented, according to embodiments.

FIG. 1A illustrates an example infrastructure for generating a three-dimensional model of a patient-specific tumor and simulating the patient-specific tumor's behavior over time, according to an embodiment. The infrastructure may comprise a platform 110 (e.g., one or more servers) which hosts and/or executes one or more of the various functions, processes, methods, and/or software modules described herein. Platform 110 may comprise dedicated servers, or may instead comprise cloud instances, which utilize shared resources of one or more servers. These servers or cloud instances may be collocated and/or geographically distributed. Platform 110 may also comprise or be communicatively connected to a server application 112 and/or one or more databases 114. In addition, platform 110 may be communicatively connected to one or more user systems 130 via one or more networks 120. Platform 110 may also be communicatively connected to one or more external systems 140 (e.g., other platforms, websites, etc.) via one or more networks 120.

Network(s) 120 may comprise the Internet, and platform 110 may communicate with user system(s) 130 through the Internet using standard transmission protocols, such as HyperText Transfer Protocol (HTTP), HTTP Secure (HTTPS), File Transfer Protocol (FTP), FTP Secure (FTPS), Secure Shell FTP (SFTP), and the like, as well as proprietary protocols. While platform 110 is illustrated as being connected to various systems through a single set of network(s) 120, it should be understood that platform 110 may be connected to the various systems via different sets of one or more networks. For example, platform 110 may be connected to a subset of user systems 130 and/or external systems 140 via the Internet, but may be connected to one or more other user systems 130 and/or external systems 140 via an intranet. Furthermore, while only a few user systems 130 and external systems 140, one server application 112, and one set of database(s) 114 are illustrated, it should be understood that the infrastructure may comprise any number of user systems, external systems, server applications, and databases.

User system(s) 130 may comprise any type or types of computing devices capable of wired and/or wireless communication, including without limitation, desktop computers, laptop computers, tablet computers, smart phones or other mobile phones, servers, game consoles, televisions, set-top boxes, electronic kiosks, point-of-sale terminals, and/or the like.

Platform 110 may comprise web servers which host one or more websites and/or web services. In embodiments in which a website is provided, the website may comprise a graphical user interface, including, for example, one or more screens (e.g., webpages) generated in HyperText Markup Language (HTML) or other language. Platform 110 transmits or serves one or more screens of the graphical user interface in response to requests from user system(s) 130. In some embodiments, these screens may be served in the form of a wizard, in which case two or more screens may be served in a sequential manner, and one or more of the sequential screens may depend on an interaction of the user or user system 130 with one or more preceding screens. The requests to platform 110 and the responses from platform 110, including the screens of the graphical user interface, may both be communicated through network(s) 120, which may include the Internet, using standard communication protocols (e.g., HTTP, HTTPS, etc.). These screens (e.g., webpages) may comprise a combination of content and elements, such as text, images, videos, animations, references (e.g., hyperlinks), frames, inputs (e.g., textboxes, text areas, checkboxes, radio buttons, drop-down menus, buttons, forms, etc.), scripts (e.g., JavaScript), and the like, including elements comprising or derived from data stored in one or more databases (e.g., database(s) 114) that are locally and/or remotely accessible to platform 110. Platform 110 may also respond to other requests from user system(s) 130.

Platform 110 may further comprise, be communicatively coupled with, or otherwise have access to one or more database(s) 114. For example, platform 110 may comprise one or more database servers which manage one or more databases 114. A user system 130 or server application 112 executing on platform 110 may submit data (e.g., user data, form data, etc.) to be stored in database(s) 114, and/or request access to data stored in database(s) 114. Any suitable database may be utilized, including without limitation MySQL™, Oracle™ IBM™, Microsoft SQL™, Access™, and the like, including cloud-based databases and proprietary databases. Data may be sent to platform 110, for instance, using the well-known POST request supported by HTTP, via FTP, and/or the like. This data, as well as other requests, may be handled, for example, by server-side web technology, such as a servlet or other software module (e.g., comprised in server application 112), executed by platform 110.

In embodiments in which a web service is provided, platform 110 may receive requests from external system(s) 140, and provide responses in eXtensible Markup Language (XML), JavaScript Object Notation (JSON), and/or any other suitable or desired format. In such embodiments, platform 110 may provide an application programming interface (API) which defines the manner in which user system(s) 130 and/or external system(s) 140 may interact with the web service. Thus, user system(s) 130 and/or external system(s) 140 (which may themselves be servers), can define their own user interfaces, and rely on the web service to implement or otherwise provide the backend processes, methods, functionality, storage, and/or the like, described herein. For example, in such an embodiment, a client application 132 executing on one or more user system(s) 130 may interact with a server application 112 executing on platform 110 to execute one or more or a portion of one or more of the various functions, processes, methods, and/or software modules described herein. Client application 132 may be "thin," in which case processing is primarily carried out server-side by server application 112 on platform 110. A basic example of a thin client application is a browser application, which simply requests, receives, and renders webpages at user system(s) 130, while the server application on platform 110 is responsible for generating the webpages and managing database functions. Alternatively, the client application may be "thick," in which case processing is primarily carried out client-side by user system(s)

130. It should be understood that client application 132 may perform an amount of processing, relative to server application 112 on platform 110, at any point along this spectrum between "thin" and "thick," depending on the design goals of the particular implementation. In any case, the application described herein, which may wholly reside on either platform 110 (e.g., in which case server application 112 performs all processing) or user system(s) 130 (e.g., in which case client application 132 performs all processing) or be distributed between platform 110 and user system(s) 130 (e.g., in which case server application 112 and client application 132 both perform processing), can comprise one or more executable software modules that implement one or more of the functions, processes, or methods of the application described herein.

1.2. Example Platform

In an embodiment, platform 110 is an interactive system which utilizes software to couple a plurality of different biological models into a simulation of how tumors (e.g., solid tumors) and their surrounding tissues (e.g., healthy tissues) respond to chemotherapeutic treatment. The tumor and its surrounding tissues may be referred to herein collectively as the "tumor microenvironment." Platform 110 may also provide a number of related software tools, including, without limitation, a graphical user interface with backend functionality that enables healthcare providers to order a simulation, configure the simulation using patient-specific data and/or other data, and/or review the results of the simulation in a clinically useful form.

Figure 1B:
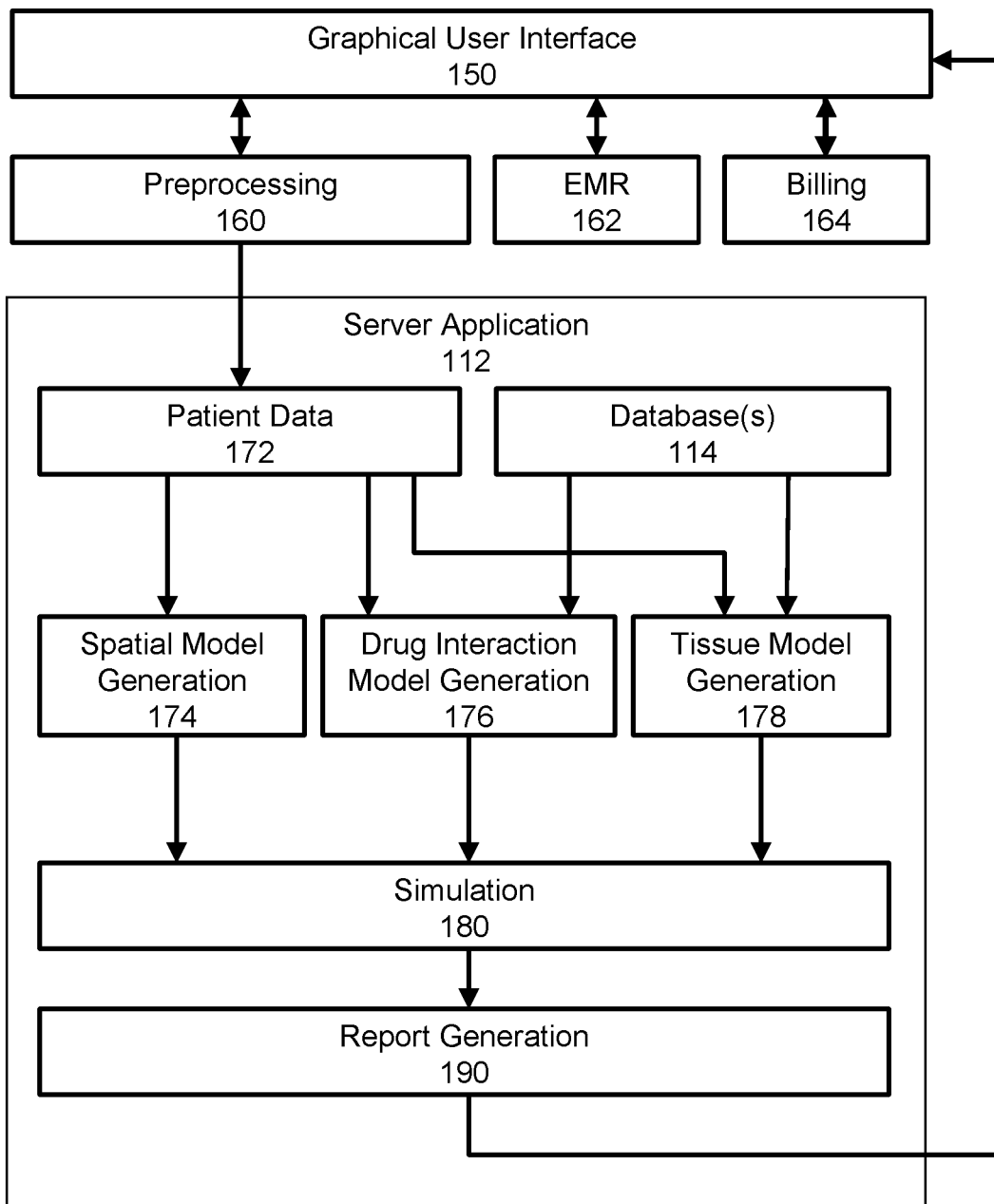

FIG. 1B illustrates an example implementation of server application 112, according to an embodiment. Specifically, FIG. 1B illustrates a graphical user interface 150, a preprocessing module 160, an electronic medical record (EMR) module 162, a billing module 164, and server application 112. Although illustrated as separate from server application 112, graphical user interface 150, preprocessing module 160, EMR module 162, and/or billing module 164 may be implemented by server application 112. Alternatively, preprocessing module 160, EMR module 162, and/or billing module 164 may be implemented as an external application that is separate and distinct from server application 112 and/or platform 110. For instance, the external application could be a stand-alone client application 132, another server application on platform 110 that is separate from server application 112, an Internet-based application on an external system 140, and/or the like. In a particular embodiment, server application 112 may provide a web service, and the external application may provide a front-end service while utilizing an API of server application 112 to perform the back-end services necessary to perform a simulation. Alternatively, the external application may generate one or more portions of graphical user interface 150 (e.g., devoted to preprocessing, EMR retrieval, and/or billing), whereas server application 112 generates a different portion of graphical user interface 150 (e.g., devoted to reporting). More generally, graphical user interface 150 may comprise a first graphical user interface generated by the external application and a second, distinct graphical user interface generated by server application 112. As mentioned elsewhere herein, server application 112 may be a cloud computing service, which utilizes shared resources that can be scaled up and down as needed.

In an embodiment, preprocessing module 160 processes data received via graphical user interface 150 prior to being used to generate simulation 180. Examples of preprocessing include, without limitation, anonymization of patient-specific data (e.g., removing patient-identifying information), "sanity" checks (e.g., to ensure that all necessary data has been collected, the collected data satisfies certain criteria, etc.), natural-language parsing or processing, and/or the like. In an embodiment in which preprocessing module 160 anonymizes patient-specific data, the advantage of implementing preprocessing function 160 in an external application, which is separate from platform 110, is that platform 100 never has access to patient-identifying information. Thus, patient confidentiality can be maintained, for example, by the healthcare provider. In an alternative embodiment in which preprocessing is not necessary, preprocessing module 160 may be omitted.

In an embodiment, EMR module 162 retrieves the patient-specific data from an EMR associated with the patient (e.g., stored at an external system 140 managed by the patient's medical provider). For example, EMR module 162 may receive a patient identifier (e.g., patient's name, patient's Social Security number (SSN) or other unique numeric or alphanumeric identifier, etc.) via graphical user interface 150 or otherwise derive the patient identifier, use the patient identifier as a key into a database of EMRs to retrieve the patient's EMR, and extract the patient-specific data from the retrieved EMR. In an alternative embodiment in which the patient-specific data is not obtained from an EMR, EMR module 162 may be omitted.

In an embodiment, billing module 164 handles payment processing, for example, related to payment for a simulation performed on platform 110. For example, billing module 164 may receive payment information directly from a user via graphical user interface 150 and/or retrieve payment information automatically (e.g., from an external system 140). In an alternative embodiment, billing module 164 may be omitted.

In the illustrated embodiment, server application 112 receives patient data 172 via preprocessing module 160 and/or directly via graphical user interface 150. Patient data 172 may be anonymized (e.g., via preprocessing module 160), to remove all patient-identifying information, such that no particular patient can be identified from patient data 172. For example, the patient's name, Social Security number, contact information, insurance information, and/or the like can be removed from patient data 172. As illustrated, server application 112 uses patient data 172 and proprietary data from database(s) 112 to construct a model of the patient's tumor microenvironment.

Figure 3:
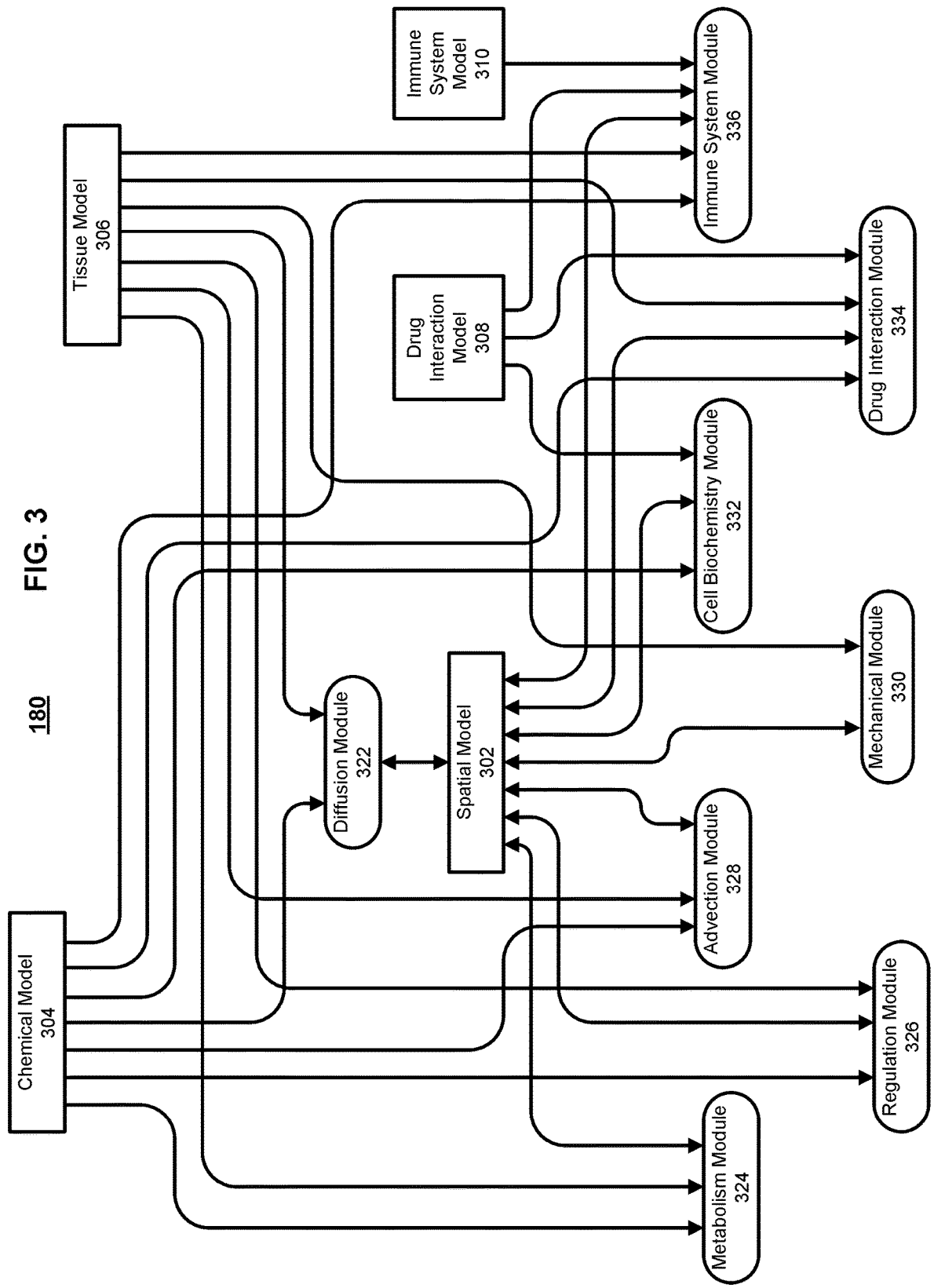
FIG. 3 is a block diagram that illustrates the various data structures that may be used in a simulation engine to simulate a patient-specific tumor, according to an embodiment.

In an embodiment, server application 112 comprises a spatial model generation module 174 that generates a spatial model (e.g., spatial model 302 in FIG. 3). Spatial model generation module 174 may generate the spatial model by segmenting one or more images in patient data 172. For example, the image(s) to be segmented by spatial model generation module 174 may comprise a three-dimensional image of the patient's tumor within its microenvironment. Using segmentation or other image processing, spatial model generation module 174 may generate a spatial model (e.g., spatial model 302 in FIG. 3) of the tumor microenvironment to be used in a simulation 180. Specifically, spatial model generation module 174 may utilize image segmentation to construct a three-dimensional representation of a patient-specific tumor microenvironment, discretized to a cubic lattice comprising a plurality of elastic material points (also referred to herein as a "site" or "location" in the spatial model). While the present description primarily refers herein to a cubic lattice, it should be understood that, in the disclosed embodiments, the cubic lattice may be replaced by a different type of structured lattice or an unstructured lattice of the tumor microenvironment. In general, a lattice is a cloud of points that are connected by a defined relationship. In a structured lattice, this defined relationship may comprise a geometric shape formed by neighboring points (e.g., a cube in the case of a cubic lattice). In another embodiment, an unstructured lattice can be used, wherein the unstructured lattice is a cloud of points with some connectivity defined among them, with no specifically defined geometric shapes.

In an embodiment, server application 112 comprises a drug interaction model generation module 176 that estimates the patient's response to one or more drugs, based on patient data 172 and proprietary model-related data in database(s) 114, and generates a patient-specific drug interaction model (e.g., drug interaction model 308 in FIG. 3) to be used in a simulation performed by simulation engine 180.

In an embodiment, server application 112 comprises a tissue model generation module 178 that generates a patient-specific metabolism model based on patient data 172 and proprietary model-related data in database(s) 114, or assigns a predefined metabolism model that suitably represents the metabolism of the patient's tissues to be simulated from a plurality of available metabolism models, stored in database(s) 114, based on patient data 172. The generated or assigned metabolism model is incorporated into a tissue model (e.g., tissue model 306 in FIG. 3), for example, along with proprietary model-related data from database(s) 114. This metabolism model, within the tissue model, may be used by a metabolism module (e.g., metabolism module 324 in FIG. 3) to generate patient-specific outputs (e.g., to spatial model 302).

In an embodiment, simulation engine 180 receives the patient-specific spatial model (e.g., 302) generated by spatial model generation module 174, the patient-specific drug interaction model (e.g., 308) generated by drug interaction model generation module 176, and the patient-specific tissue model (e.g., 306) generated by tissue model generation module 178. Simulation engine 180 may also receive other models and modules, for example, from database(s) 114. These other models and modules may be predefined (i.e., not patient-specific), or alternatively, may be generated as patient-specific models or modules using patient data 172 in a similar manner as the spatial model, drug interaction model, and/or tissue model are generated. For example, server application 112 may comprise an immune system model generation module (not shown) that generates a patient-specific immune system model (e.g., immune system model 310 in FIG. 3), from patient data 172 and/or proprietary model-related data in database(s) 114, to be used in simulation engine 180.

In an embodiment, simulation engine 180 iteratively invokes a series of one or more subroutines that advance a simulation of the tumor microenvironment, represented by the spatial model (e.g., 302), forward in time according to a time step. This series of subroutines may include, without limitation:

(1) one or more diffusion subroutines (e.g., implemented or called by diffusion module 322 in FIG. 3) that represent the diffusion of modeled chemical species, such as nutrients (e.g., oxygen, glucose, etc.), metabolic waste byproducts (e.g., ammonia, lactate, etc.), and drugs (e.g., doxorubicin, methotrexate, etc.), within the simulated tumor microenvironment;

(2) one or more subroutines (e.g., implemented or called by advection module 328, cell biochemistry module 332, and/or drug interaction module 334 in FIG. 3) that represent the uptake or efflux of modeled chemical species by modeled tissues at each lattice site, either passively or actively (e.g., via known transporters);

(3) one or more subroutines (e.g., implemented or called by metabolism module 324 in FIG. 3) that represent the metabolic behavior of the modeled tissues at each lattice site (e.g., using flux balance analysis (FBA));

(4) one or more subroutines (e.g., implemented or called by mechanical module 330 in FIG. 3) that represent the expansion and/or contraction of the modeled tissues in response to their growth and/or death rates at each lattice site;

(5) one or more subroutines (e.g., implemented or called by regulation module 326 in FIG. 3) that represent the regulatory response of the modeled tissues to local chemical concentrations; and/or (6) one or more subroutines (e.g., implemented or called by immune system module 336 in FIG. 3) that represent the behavior of a modeled immune system in response to the local microenvironmental conditions (e.g., immune-modulating drugs).

In an embodiment, server application 112 comprises a report generation module 190 that generates a report based on the results of simulation engine 180. The report may comprise statistics (e.g., measurements of the tumor over time in tabular, graphical, or other form), two-dimensional representation(s) (e.g., two-dimensional image) of the tumor microenvironment over time, three-dimensional representation(s) (e.g., three-dimensional image) of the tumor microenvironment over time, and/or the like. The report may be rendered in graphical user interface 150, for example, in the same or separate graphical user interface by which patient and/or billing data was received. Alternatively or additionally, the report may be converted into a file (e.g., Portable Document Format (PDF) file, spreadsheet file, comma-separated values (CSV) file or other text file, etc.) that may be printed, emailed, and/or the like, and/or otherwise provided to a user (e.g., patient or healthcare provider).

1.3. Example Processing Device

Figure 2:
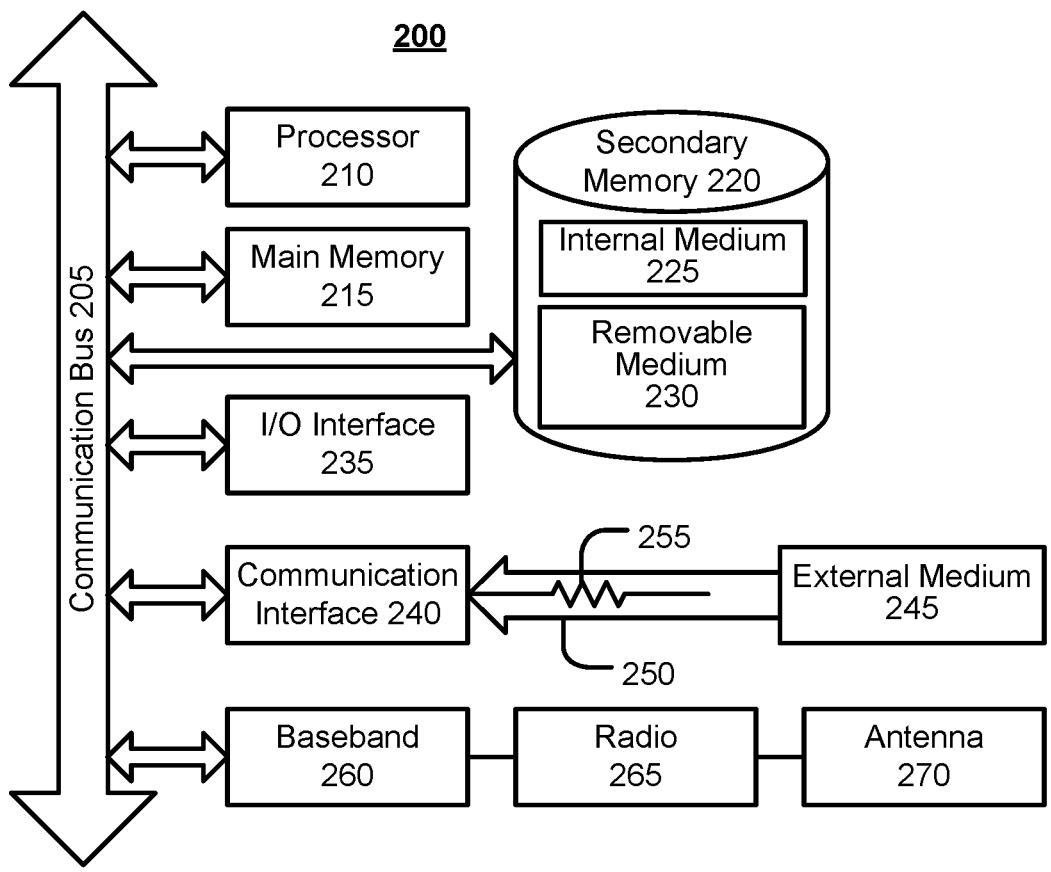
FIG. 2 is a block diagram that illustrates an example processing system, by which one or more of the processed described herein, may be executed, according to an embodiment.

FIG. 2 is a block diagram illustrating an example wired or wireless system 200 that may be used in connection with various embodiments described herein. For example, system 200 may be used as or in conjunction with one or more of the functions, processes, or methods (e.g., to store and/or execute the application or one or more software modules of the application) described herein, and may represent components of platform 110, user system(s) 130, external system(s) 140, and/or other processing devices described herein. System 200 can be a server or any conventional personal computer, or any other processor-enabled device that is capable of wired or wireless data communication. Other computer systems and/or architectures may be also used, as will be clear to those skilled in the art.

System 200 preferably includes one or more processors, such as processor 210. Additional processors may be provided, such as an auxiliary processor to manage input/output, an auxiliary processor to perform floating-point mathematical operations, a special-purpose microprocessor having an architecture suitable for fast execution of signal-processing algorithms (e.g., digital-signal processor), a slave processor subordinate to the main processing system (e.g., back-end processor), an additional microprocessor or controller for dual or multiple processor systems, and/or a coprocessor. For example, one or more graphics processing units (GPUs) may be used to perform mathematical computations for the simulations performed by simulation engine 180. Such auxiliary processors may be discrete processors or may be integrated with processor 210. Examples of processors which may be used with system 200 include, without limitation, the Pentium® processor, Core i7® processor, and Xeon® processor, all of which are available from Intel Corporation of Santa Clara, Calif.

Processor 210 is preferably connected to a communication bus 205. Communication bus 205 may include a data channel for facilitating information transfer between storage and other peripheral components of system 200. Furthermore, communication bus 205 may provide a set of signals used for communication with processor 210, including a data bus, address bus, and/or control bus (not shown). Communication bus 205 may comprise any standard or non-standard bus architecture such as, for example, bus architectures compliant with industry standard architecture (ISA), extended industry standard architecture (EISA), Micro Channel Architecture (MCA), peripheral component interconnect (PCI) local bus, standards promulgated by the Institute of Electrical and Electronics Engineers (IEEE) including IEEE 488 general-purpose interface bus (GPIB), IEEE 696/S-100, and/or the like.

System 200 preferably includes a main memory 215 and may also include a secondary memory 220. Main memory 215 provides storage of instructions and data for programs executing on processor 210, such as one or more of the functions and/or modules discussed herein. It should be understood that programs stored in the memory and executed by processor 210 may be written and/or compiled according to any suitable language, including without limitation C/C++, Java, JavaScript, Perl, Visual Basic, .NET, and the like. Main memory 215 is typically semiconductor-based memory such as dynamic random access memory (DRAM) and/or static random access memory (SRAM). Other semiconductor-based memory types include, for example, synchronous dynamic random access memory (SDRAM), Rambus dynamic random access memory (RDRAM), ferroelectric random access memory (FRAM), and the like, including read only memory (ROM).

Secondary memory 220 may optionally include an internal medium 225 and/or a removable medium 230. Removable medium 230 is read from and/or written to in any well-known manner. Removable storage medium 230 may be, for example, a magnetic tape drive, a compact disc (CD) drive, a digital versatile disc (DVD) drive, other optical drive, a flash memory drive, and/or the like.

Secondary memory 220 is a non-transitory computer-readable medium having computer-executable code (e.g., disclosed software modules) and/or other data stored thereon. The computer software or data stored on secondary memory 220 is read into main memory 215 for execution by processor 210.

In alternative embodiments, secondary memory 220 may include other similar means for allowing computer programs or other data or instructions to be loaded into system 200. Such means may include, for example, a communication interface 240, which allows software and data to be transferred from external storage medium 245 to system 200. Examples of external storage medium 245 may include an external hard disk drive, an external optical drive, an external magneto-optical drive, and/or the like. Other examples of secondary memory 220 may include semiconductor-based memory, such as programmable read-only memory (PROM), erasable programmable read-only memory (EPROM), electrically erasable read-only memory (EEPROM), and flash memory (block-oriented memory similar to EEPROM).

As mentioned above, system 200 may include a communication interface 240. Communication interface 240 allows software and data to be transferred between system 200 and external devices (e.g. printers), networks, or other information sources. For example, computer software or executable code may be transferred to system 200 from a network server (e.g., platform 110) via communication interface 240. Examples of communication interface 240 include a built-in network adapter, network interface card (NIC), Personal Computer Memory Card International Association (PCMCIA) network card, card bus network adapter, wireless network adapter, Universal Serial Bus (USB) network adapter, modem, a wireless data card, a communications port, an infrared interface, an IEEE 1394 fire-wire, and any other device capable of interfacing system 200 with a network (e.g., network(s) 120) or another computing device. Communication interface 240 preferably implements industry-promulgated protocol standards, such as Ethernet IEEE 802 standards, Fiber Channel, digital subscriber line (DSL), asynchronous digital subscriber line (ADSL), frame relay, asynchronous transfer mode (ATM), integrated digital services network (ISDN), personal communications services (PCS), transmission control protocol/Internet protocol (TCP/IP), serial line Internet protocol/point to point protocol (SLIP/PPP), and so on, but may also implement customized or non-standard interface protocols as well.

Software and data transferred via communication interface 240 are generally in the form of electrical communication signals 255. These signals 255 may be provided to communication interface 240 via a communication channel 250. In an embodiment, communication channel 250 may be a wired or wireless network (e.g., network(s) 120), or any variety of other communication links. Communication channel 250 carries signals 255 and can be implemented using a variety of wired or wireless communication means including wire or cable, fiber optics, conventional phone line, cellular phone link, wireless data communication link, radio frequency ("RF") link, or infrared link, just to name a few.

Computer-executable code (e.g., computer programs, such as the disclosed application, or software modules) is stored in main memory 215 and/or secondary memory 220. Computer programs can also be received via communication interface 240 and stored in main memory 215 and/or secondary memory 220. Such computer programs, when executed, enable system 200 to perform the various functions of the disclosed embodiments as described elsewhere herein.

In this description, the term "computer-readable medium" is used to refer to any non-transitory computer-readable storage media used to provide computer-executable code and/or other data to or within system 200. Examples of such media include main memory 215, secondary memory 220 (including internal memory 225, removable medium 230, and external storage medium 245), and any peripheral device communicatively coupled with communication interface 240 (including a network information server or other network device). These non-transitory computer-readable media are means for providing executable code, programming instructions, software, and/or other data to system 200.

In an embodiment that is implemented using software, the software may be stored on a computer-readable medium and loaded into system 200 by way of removable medium 230, I/O interface 235, or communication interface 240. In such an embodiment, the software is loaded into system 200 in the form of electrical communication signals 255. The software, when executed by processor 210, preferably causes processor 210 to perform one or more of the processes and functions described elsewhere herein.

In an embodiment, I/O interface 235 provides an interface between one or more components of system 200 and one or more input and/or output devices. Example input devices include, without limitation, sensors, keyboards, touch screens or other touch-sensitive devices, biometric sensing devices, computer mice, trackballs, pen-based pointing devices, and/or the like. Examples of output devices include, without limitation, other processing devices, cathode ray tubes (CRTs), plasma displays, light-emitting diode (LED) displays, liquid crystal displays (LCDs), printers, vacuum fluorescent displays (VFDs), surface-conduction electron-emitter displays (SEDs), field emission displays (FEDs), and/or the like. In some cases, an input and output device may be combined, such as in the case of a touch panel display (e.g., in a smartphone, tablet, or other mobile device).

System 200 may also include optional wireless communication components that facilitate wireless communication over a voice network and/or a data network (e.g., in the case of user system 130). The wireless communication components comprise an antenna system 270, a radio system 265, and a baseband system 260. In system 200, radio frequency (RF) signals are transmitted and received over the air by antenna system 270 under the management of radio system 265.

In an embodiment, antenna system 270 may comprise one or more antennae and one or more multiplexors (not shown) that perform a switching function to provide antenna system 270 with transmit and receive signal paths. In the receive path, received RF signals can be coupled from a multiplexor to a low noise amplifier (not shown) that amplifies the received RF signal and sends the amplified signal to radio system 265.

In an alternative embodiment, radio system 265 may comprise one or more radios that are configured to communicate over various frequencies. In an embodiment, radio system 265 may combine a demodulator (not shown) and modulator (not shown) in one integrated circuit (IC). The demodulator and modulator can also be separate components. In the incoming path, the demodulator strips away the RF carrier signal leaving a baseband receive audio signal, which is sent from radio system 265 to baseband system 260.

If the received signal contains audio information, then baseband system 260 decodes the signal and converts it to an analog signal. Then the signal is amplified and sent to a speaker. Baseband system 260 also receives analog audio signals from a microphone. These analog audio signals are converted to digital signals and encoded by baseband system 260. Baseband system 260 also encodes the digital signals for transmission and generates a baseband transmit audio signal that is routed to the modulator portion of radio system 265. The modulator mixes the baseband transmit audio signal with an RF carrier signal, generating an RF transmit signal that is routed to antenna system 270 and may pass through a power amplifier (not shown). The power amplifier amplifies the RF transmit signal and routes it to antenna system 270, where the signal is switched to the antenna port for transmission.

Baseband system 260 is also communicatively coupled with processor 210, which may be a central processing unit (CPU). Processor 210 has access to data storage areas 215 and 220. Processor 210 is preferably configured to execute instructions (i.e., computer programs, such as the disclosed application, or software modules) that can be stored in main memory 215 or secondary memory 220. Computer programs can also be received from baseband processor 260 and stored in main memory 210 or in secondary memory 220, or executed upon receipt. Such computer programs, when executed, enable system 200 to perform the various functions of the disclosed embodiments.

1.4. Example Data Structures

FIG. 3 is a block diagram that illustrates the various data structures that may be used in simulation engine 180 to simulate a patient-specific tumor, according to an embodiment. In the illustrated embodiment, simulation engine 180 comprises a combination of interconnected models and modules. The modules operate on the models (e.g., call subroutines implemented by the models to get, set, or otherwise operate on data stored by the models) to perform simulations.

The models comprise one or more spatial models 302, one or more chemical models 304, one or more tissue models 306, one or more drug interaction models 308, and/or one or more immune system models 310. In a typical implementation, only one spatial model 302 will be necessary, whereas a plurality of chemical models 304, a plurality of tissue models 306, a plurality of drug interaction models 308, and a plurality of immune system models 310 will be used. For the sake of simplicity, each model will be referred to herein in the singular. However, it should be understood that each model may comprise one or a plurality of distinct models (e.g., for distinct volumes or other spaces with respect to spatial model 302, for distinct chemicals with respect to chemical model 304, for distinct tissues types with respect to tissue model 306, for distinct drugs with respect to drug interaction model 308, and/or for distinct components and/or behaviors of the immune system for immune system model 310). Each model stores information regarding the state of a dynamic component in the simulation, and the behavior of that dynamic component within the simulation (i.e., how the dynamic component may be updated). It should be understood that each model attempts to replicate the behavior of an actual physical feature (e.g., a tumor, tissue, chemical, drug, etc.) for use in the simulation, and may comprise sub-models that model certain properties, behaviors, interactions, and/or the like.

In the illustrated embodiment, the modules comprise a diffusion module 322, a metabolism module 324, a regulation module 326, an advection module 328, a mechanical module 330, a cell biochemistry module 332, a drug interaction module 334, and an immune system module 336. Each module receives and integrates data from one or more of the models to iteratively update the simulation through a plurality of time steps. For example, each module may receive data from one or more models 302-310 and utilize that data to update one or more locations within a tumor and/or microenvironment of the tumor represented in spatial model 302. For example, the module may update a chemical property and/or tissue property at each location.

Not all of the illustrated models and modules are necessary in all embodiments. For instance, in an alternative embodiment, immune system model 310 and immune system module 336 may be omitted. In other alternative embodiments, other models and/or modules may be omitted.

1.4.1. Spatial Model

In an embodiment, spatial model 302 stores information about one or more properties of each chemical (e.g., modeled by chemical model 304) and each tissue (e.g., modeled by tissue model 306) at each material point in the lattice (e.g., cubic lattice) representing the simulation volume. For each chemical, spatial model 302 may, for example, store concentrations of the chemical at each location. For each tissue, spatial model 302 may, for example, store the densities, mechanical properties, and regulatory state of the tissue at each location.

In an embodiment, spatial model 302 treats the modeled tissues as a lattice (e.g., cubic lattice) of elastic material points that can expand or stretch and contract or shrink. Tissues in different regions may grow or die at different rates, such that the volume and shape of the tissue may change over time. Each material point in the lattice of spatial model 302 may be treated as though it is connected to each of its neighboring material points by a set of springs. Each spring has a natural length value and stiffness value associated with it (e.g., stored as mechanical properties for the tissue). The stiffness value can be used to represent differences between tissue types, such as adipose tissue and solid tumor tissue. As the tissue at a given material point expands or contracts, the lengths of the springs between that material point and its neighboring material points increase or decrease accordingly. Each time the spring lengths change for a given material point, mechanical module 330 may re-compute the mechanical forces at each material point and update their locations accordingly. This is performed multiple times until the forces reach equilibrium such that the material points stop moving. This type of model is generally referred to as a mass spring model, which is described in "A new optimization approach for mass-spring models parameterization," by da Silva et al., Graphical Models, 81:1-17 (2015), and "Mass spring models with adjustable Poisson's ratio," by Kot et al., The Visual Computer, 33(3):283-291 (2017) ("Kot et al."), which are both hereby incorporated herein by reference as if set forth in full. However, it should be understood that other models for approximating the mechanics of deformable materials may be implemented by spatial model 302, including, without limitation, finite element methods, the material point method, and/or the like.

In an embodiment, from time to time during the simulation, the material points in the lattice of the simulation volume may be "regridded" by constructing a new set of material points, each with springs of equal length, such that they exhibit the same shape and density as that of the previously deformed set of material points. This occasional re-gridding process may increase the simulation's performance.

Spatial model 302 is operated upon by diffusion module 322, metabolism module 324, regulation module 326, advection module 328, mechanical module 330, cell biochemistry module 332, drug interaction module 334, and/or immune system module 336. These operations may comprise the module receiving (e.g., retrieving) data from spatial model 302 as well as updating and otherwise operating upon data in spatial model 302. For example, a particular module may iteratively receive one or more chemical properties (e.g., concentration) and/or one or more tissue properties (e.g., density, permeability, regulatory state, etc.) at each location in spatial model 302, and then utilize those received properties (e.g., with other data) to iteratively update one or more chemical and/or tissue properties at each location in spatial model 302.

1.4.2. Chemical Model

In an embodiment, each chemical model 304 replicates the behavior of a chemical or chemical species (referred to herein simply as a "chemical") that is present in the simulation (e.g., represented at one or more material points in spatial model 302). For example, each chemical model 304 may provide information about one or more properties of its respective chemical, such as the chemical's diffusion rate, boundary values, and/or the like. Chemical model 304 provides this information to diffusion module 322, metabolism module 324, regulation module 326, advection module 328, cell biochemistry module 332, drug interaction module 334, and/or immune system module 336.

Each chemical model 304 (e.g., representing a different chemical species, including nutrients, drugs, diffusible signaling factors, etc.), used for a particular simulation, may be implemented as an instance of a chemical class. The chemical class may comprise data structures (e.g., variables and subroutines) for one or more of the following:

(1) data describing the concentration of the chemical at every location within the simulation volume (e.g., cubic lattice) of spatial model 302.

(2) parameters related to the chemical's transport dynamics, including the chemical's diffusion rate.

(3) data describing the boundary values of the chemical concentrations, including those on the outermost limits of the simulation volume and those corresponding to regions representing vascular tissue.

(4) zero or more models (and related data) that describe the time-dependence of the chemical concentrations in the blood and/or other tissues. For example, such models may include, without limitation, a multi-compartment pharmacokinetic model of the plasma concentration of a drug, parameters describing a multi-exponential fit to such a pharmacokinetic model and/or describing variations in the blood glucose concentration of a patient in response to changes in diet and/or other lifestyle factors, and/or the like.

Chemicals can be produced, consumed, or otherwise transformed by the tissues (e.g., represented by tissue model 306). Depending on the local concentrations of the chemicals, the local density of the tissue, and the tissue's regulatory state, chemical reactions can occur at different local rates. These local rates may be represented by chemical model 304 in any number of functional forms. In a simple example, the local rates may be represented as the product of some constant and the local density of tissue in a given regulatory state, which might describe the production of a signaling molecule.

As another example, the local rates may be represented using Michaelis-Menten kinetics, which might be used to model the transporter-mediated internalization of a nutrient or drug. For instance, a Michaelis-Menten-type chemical reaction can be represented by the following equations:

$$\varphi_{ext}(x, t + \Delta t) = \varphi_{ext}(x, t) - k(x, t)\Delta t$$

$$\varphi_f(x, t + \Delta t) = \varphi_f(x, t) - k(x, t)\Delta t$$

$$k(x, t) = \rho(x, t)\frac{Ek_{cat}}{V_{cell}}\frac{\varphi_{ext}(x, t)}{k_m + \varphi_{ext}(x, t)}$$

wherein $\varphi_{ext}(x, t)$ and $\varphi_{17}(x, t)$ are the instantaneous local concentrations of the extracellular and intracellular forms of a chemical, respectively, wherein $\Delta t$ is the time step, wherein $k(x, t)$ represents the instantaneous local uptake rate, wherein $\rho(x, t)$ represents the instantaneous local cell volume fraction, E represents the number of enzymatic transporters on a cell membrane, $V_{cell}$ represents the volume of a cell, $k_{cat}$ represents the enzyme turnover rate, and $k_m$ is the so-called Michaelis constant for the reaction.

1.4.3. Tissue Model

In an embodiment, each tissue model 306 replicates the behavior of a tissue that is present in the simulation (e.g., represented at one or more locations in the simulation volume of spatial model 302). For example, each tissue model 306 may produce information about one or more properties of its respective tissue, such as that tissue's metabolic properties, mechanical properties, transitions between regulatory states, and/or the like. Tissue model 306 provides this information to diffusion module 322, metabolism module 324, regulation module 326, advection module 328, mechanical module 330, drug interaction module 334, and/or immune system module 336.

Each tissue model 306 (e.g., representing a different tissue), used for a particular simulation, may be implemented as an instance of a tissue class. The tissue class may comprise data structures (e.g., variables and subroutines) for one or more of the following:

(1) data describing the location, shape, density, and/or mechanical properties (e.g., elastic moduli) of the tissue.

(2) data describing the regulatory state of the tissue (e.g., normoxic, hypoxic, etc.) at each location.

(3) zero or more models (and related data) that compute the rate of chemical reactions carried out by the tissue (e.g., production of chemicals, consumption of chemicals, internalization of chemicals, etc.) at each location, as a function of the local concentrations of chemicals and of the tissue's local regulatory state and density. As one example, at least one of these models may describe the production rate of vascular endothelial growth factor (VEGF) by cancer cells under hypoxic conditions. In such a case, low levels of oxygen may drive the tissue cells to transition to a hypoxic regulatory state at some rate (e.g., defined by a model that computes the regulatory response of the tissue, as described elsewhere herein), and these hypoxic cells may then produce VEGF at some other rate. As another example, at least one of these models may describe the uptake kinetics, for each of a plurality of different metabolites (e.g., glucose, lactate, etc.), which might transform a diffusible extracellular version of the metabolite into a non-diffusible intracellular version of the metabolite.

(4) zero or more models (and related data) that compute the metabolic response of the tissue to one or more chemicals at each location, as a function of the local concentrations of chemicals and of the tissue's local regulatory state. As an example, at least one of these models may describe the metabolism of the simulated tissues at each location. FBA could be used to predict the metabolic behavior of a given tissue cell type under a range of environmental conditions. Such a model can be used, for example, by the metabolism module 324, along with concentrations of different chemicals (e.g., glucose, oxygen, etc.), to compute the consumption rates of the chemicals by the nearby tissues at each location, as well as the tissues' local growth rates at each location.

(5) zero or more models (and related data) that compute the regulatory response (e.g., transitions rates between regulatory states) of the tissue at each location, as a function of the local values of one or more regulatory effectors (e.g., chemical species, including nutrients, metabolic byproducts, and/or signaling molecules, as well as mechanical properties, including stresses, strains, and/or tissue densities, etc.). As discussed above, at least one of these models may describe the transition between normoxic and hypoxic regulatory states of tissue at each location. Under hypoxic conditions, hypoxia-inducible factor (HIF-1a) can become active, leading to a cascade of intracellular signals that can reprogram metabolism and lead to the production of a number of pro-angiogenic molecules. The transition rates between such regulator states may be described in terms of Hill-type functions or in more complex terms, depending on the detail of the model. As another example, at least one of these models may account for biomechanical cues that influence mitogen-activated protein kinases (MAPK) signaling, which can play a critical role in controlling cell growth and proliferation. In either case, these models may comprise mathematical descriptions of the rates at which regulatory transitions occur, and can be used by regulation module 326 to update the regulatory state of the tissues at every location.

In an embodiment, FBA is used to predict the metabolic behavior and growth rates of tissues at each location in the simulation volume for each iteration of the simulation. FBA is described in "What is flux balance analysis?," by Orth et al., Nature Biotechnology, 28(3):245 (2010), which is hereby incorporated herein by reference as if set forth in full. In addition, one use of FBA in a spatially-resolved and time-dependent manner is described in "Metabolic resource allocation in individual microbes determines ecosystem interactions and spatial dynamics," by Harcombe et al., Cell Rep., 7(4):1104-15 (2014) ("Harcombe et al."), which is hereby incorporated herein by reference as if set forth in full. However, Harcombe et al. used two-dimensional models, were focused on microbial species on agar plates, and assumed that cell material expands diffusively, instead of elastically. In contrast, disclosed embodiments utilize a three-dimensional model, focused on a tumor microenvironment, that assumes that tissue expand and contract elastically.

Cellular metabolism is a complex process involving thousands of chemical reactions, which effectively enable cells to extract energy and chemical building blocks from their surroundings and use them to grow and survive. Because cells of different types and in different regulatory states express different sets of enzymes, the details of the chemical pathways that are used can vary from tissue to tissue and regulatory state to regulatory state. In an embodiment, tissue model 306 uses FBA as a metabolism model to predict the local consumption and production rates of the various metabolites in the simulation and the growth rate of the local tissues in the simulation. FBA can be used in a similar manner as described in "Spatially-resolved metabolic cooperativity within dense bacterial colonies," by Cole et al., BMC Systems Biology, 9(1):15 (2015) ("Cole et al."), which is hereby incorporated herein by reference as if set forth in full.

Similarly to Harcombe et al., Cole et al. also focused on microbial colonies on agar plates. However, Cole et al. describes how to model both active and passive uptake of chemical species by modeled cells. Cole et al. also describes using a precomputed table of FBA solutions and a scheme for interpolating among the FBA solutions, in order to speed up the calculation of the metabolic behavior of the cells in every location. Cole et al. further describes the ability of cells to switch between regulatory states based on local chemical concentrations. All of these methods may be implemented by tissue model 306 to predict the cellular growth rates and metabolic behaviors of the represented tissues. Alternatively, tissue model 306 may utilize other methods of predicting cellular growth rates and metabolic behaviors of the represented tissues.

1.4.4. Drug Interaction Model

In an embodiment, each drug interaction model 308 replicates the behavior of one or more drugs' impact on one or more tissues. For example, each drug interaction model 308 may produce information about one or more properties of its respective drug for each of one or more types of tissue, such as that drug's rate of internationalization for each tissue type, lethal intracellular concentrations for each tissue type, the rate at which the drug kills tumor tissues, and/or the like. Drug interaction model 308 provides this information to cell biochemistry module 332, drug interaction module 334, and/or immune system module 336.

For example, drugs of different classes can have very different mechanisms of action. A mathematical model, describing a drug's activity, can be tailored to each drug to be simulated. These drug-specific models may be implemented as global descriptions of the drugs' interactions, and used by drug interaction module 334 to compute drug-related kinetics at each location in the simulation volume of spatial model 302.

As an illustrative example, compare the difference between the modes of action of trastuzumab and doxorubicin. Trastuzumab binds cancer cell surface receptors (HER2) and recruits immune effector cells to kill the cancer cells, whereas doxorubicin is internalized, intercalates into the DNA, prevents replication, and leads to cell death.

A model of trastuzumab may specify the kinetic binding and unbinding rates of the drug to the receptors and a functional representation of the rate of cancer cell death caused by the immune effector cells (e.g., in terms of a Hill-type function). The model of trastuzumab may also specify which variables need to be accessed in order to compute the relevant rates. These variables may include, for example, the concentrations of the free and bound cell surface receptors, the immune cell density, and/or the like.

A model of doxorubicin may include kinetic parameters for the uptake and efflux of the drug by different tissue cells. This may be described by Michaelis-Menten kinetics and a functional representation of the rate of tissue death in terms of the intracellular concentration of the drug. The model of doxorubicin may specify the pertinent variables, including the extracellular and intracellular drug concentrations, as well as the tissues' proliferation rates since doxorubicin is selective for proliferating tissue cells.

1.4.5. Immune System Model

In an embodiment, each immune system model 310 replicates a behavior of the immune system in response to the microenvironmental conditions of the tumor being simulated (e.g., represented in spatial model 302) and/or immuno-therapeutics. For example, each immune system model 310 may produce information about the immune system's behavior, such as T-cell mobility, activation parameters, and/or the like. In an embodiment, immune system model 310 provides such information to immune system module 336.

Within immune system model 310, T-cells may be modeled as individual motile agents. These agents may be governed by an agent-based simulation scheme, and may transition between activation states and kill target cells in response to the local tissues' phenotypic and/or mechanical states, and/or the local concentrations of drugs and other chemicals. For example, immune system model 310 may utilize one or more of the models described in U.S. Patent Pub. Nos. 2003/0104475, published on Jun. 5, 2003, and 2005/0055188, published on Mar. 10, 2005, "Discovery of cancer vaccination protocols with a genetic algorithm driving an agent based simulator," by Lollini et al., BMC Bioinformatics, 7(1):352 (2006), "Modeling the competition between lung metastases and the immune system using agents," by Pennisi et al., BMC Bioinformatics, 11(Suppl. 7):S13 (2010), "Modeling Protective Anti-Tumor Immunity via Preventative Cancer Vaccines Using a Hybrid Agent-based and Delay Differential Equation Approach," by Kim et al., PLoS Computational Biology, 8(10):e1002742 (2012), "Simulating cancer growth with multiscale agent-based modeling," by Wang et al., Seminars in Cancer Biology, 30:70-78 (2015), and "A computational multiscale agent-based model for simulating spatio-temporal tumour immune response to pd1 and pdl1 inhibition," by Gong et al., Journal of the Royal Society Interface, 14(134):20170320 (2017), which are all hereby incorporated herein by reference as if set forth in full.

1.4.6. Diffusion Module

In an embodiment, diffusion module 322 updates one or more properties (e.g., concentrations) of each chemical (e.g., modeled by chemical model 304) at one or more locations within spatial model 302 and/or updates properties (e.g., permeabilities, densities, etc.) of each tissue (e.g., modeled by tissue model 306) at one or more locations within spatial model 302. Diffusion module 322 receives information from spatial model 302, chemical model 304, and/or tissue model 306, and provides information to spatial model 302. For example, diffusion module 322 may, in one iteration of the simulation, receive information regarding the current concentrations of chemical(s) and/or tissue densities at one or more locations from spatial model 302 and the diffusion rates and/or boundary values of those chemicals from chemical model 304, and use that information to update the concentrations of chemical(s) at the location(s) within spatial model 302 in a subsequent iteration of the simulation. Similarly, diffusion module 322 may receive information regarding one or more properties of tissue(s) from tissue model 306, and use that information to update the one or more tissue properties at one or more locations within spatial model 302.

In an embodiment, the diffusion of each chemical is modeled using a finite difference scheme. For a given location in the simulation volume of spatial model 302, the concentration of the chemical at time t+Δt is expressed in terms of the concentrations of the chemical at that location and its nearest neighbors at time t. The number of neighbors to be utilized can be any number (e.g., the six nearest neighbors, the twenty-seven nearest neighbors, etc.). However, a larger number will generally provide greater stability and allow for longer values of Δt. Other schemes that may be used to model chemical diffusion include, without limitation, a finite element scheme, a finite volume scheme, a meshless/meshfree scheme, a domain decomposition scheme, and a stochastic partial differential equation scheme.

In an embodiment, the diffusion coefficient of each chemical is not necessarily assumed to be constant. For example, depending on the tissue through which the chemical is diffusing and that tissue's density, the chemical may undergo hindered diffusion. If the chemical is internalized by the local tissue (e.g., which may be the case for many drugs), the chemical may not diffuse at all. Diffusion module 322 may account for these types of anisotropies in the diffusion coefficient, for example, using a similar method as disclosed in Cole et al. Specifically, the effective diffusion rates of hindered chemicals may be given approximately by:

$$D_{\text{eff}}(x, t) = \frac{1 - \rho(x, t)}{1 + \frac{\rho(x, t)}{2}} D$$

wherein D is the diffusion rate of the chemical in water and $\rho(x, t)$ is the instantaneous local cell volume fraction at the location x. Alternatively, other schemes for modifying the diffusion coefficient are possible.

Diffusion at each location may be modeled using a seven-point stencil finite difference approach. The extracellular concentration of a chemical $\varphi$ at location i is updated as:

$$\varphi_i(t + \Delta t) = \varphi_i(t) + \frac{\Delta t}{\lambda} \sum_j J_{\varphi j \to i}(t)$$

$$J_{\varphi j \to i}(t) = \frac{D_{\varphi j}(t) + D_{\varphi i}(t)}{2} \frac{\varphi_j(t) - \varphi_i(t)}{\lambda}$$

wherein $\lambda$ is the lattice spacing between lattice sites, j indexes over the six lattice sites neighboring site i, $J_{\varphi j \to i}(t)$ represents the diffusive flux across the boundary separating sites j and i, $D_{\varphi i}$ and $D_{\varphi j}$ are the diffusion coefficients for the chemicals in lattice sites i and j, respectively. Notably, the diffusion coefficients for lattice sites i and j are averaged to ensure continuity when $D_{\varphi i} \neq D_{\varphi j}$. The maximum theoretical value for $\Delta t$ is $$\frac{\lambda}{2D_{o_2}},$$

which is approximately $2 \times 10^{-2}$ seconds. However, in an embodiment, a more conservative value of $1 \times 10^{-3}$ seconds is used in order to ensure convergence.

1.4.7. Metabolism Module

In an embodiment, metabolism module 324 updates one or more properties (e.g., concentrations) of chemical(s) and/or one or more properties (e.g., growth rates) of tissue(s) at one or more locations in the simulation volume of spatial model 302, to reflect the metabolic behavior of the tissue(s). Metabolism module 324 may receive inputs from spatial model 302, chemical model 304, and/or tissue model 306, and update spatial model 302 based on these inputs. For example, metabolism module 324 may receive the concentrations of chemical(s) at one or more locations from spatial model 302, one or more properties of chemical(s) from chemical model 304, and/or the metabolism of tissue(s) from tissue model 306, and use this information to update the chemical concentrations and/or growth rates of tissue(s) at one or more material points in the lattice of spatial model 302.

In an embodiment, the metabolic capabilities of each tissue are described using FBA. In this case, the concentrations of each metabolite at a given location can be used to form an upper bound on each metabolite's respective uptake rate by each tissue. These upper bounds are proportional to $\varphi_i/\Delta t$, wherein $\varphi_i$ represents the local concentration of metabolite i, and $\Delta t$ represents the time step of the simulation. Each upper bound ensures that the local tissue cannot take up more of a given metabolite than is available at each location. With these upper bounds set, FBA can be used to predict the optimal set of reaction fluxes throughout a tissue's metabolic network.

Optimality in this case may be defined differently for different tissues. For a tumor, the optimal set of fluxes may be assumed to be the one that leads to fastest growth with minimal total flux (so-called "parsimonious" FBA). For adipocytes or other tissue types that do not proliferate uncontrollably, optimality may be defined in terms of the minimal total flux necessary to maintain suitable intracellular adenosine triphosphate (ATP) concentrations. In either case, the uptake and efflux fluxes, predicted by FBA, can be used to update the local concentrations of the metabolites at each location in the simulation volume of spatial model 302. For example, if metabolite i at some location was predicted to be consumed at a rate v, then metabolite i's local concentration would be updated as $\varphi_i \leftarrow \varphi_i + v \cdot \Delta t$. Moreover, because FBA also elicits predictions of the local tissue's growth rate g (assuming that the local tissue is indeed growing), then the local tissue's density $\psi$ can be updated as $\psi_i \leftarrow \psi_i \cdot e^{g \cdot \Delta t}$.

Because FBA requires the linear optimization of a system involving thousands of reactions and needs to be performed at every location in the simulation volume, FBA can be computationally expensive. Thus, as an alternative to dynamic FBA, FBA solutions can be precomputed, for a range of metabolites concentrations, prior to runtime, and incorporated into a lookup table to be used during runtime. Metabolism module 324 can perform lookups in this precomputed lookup table to identify the appropriate FBA solution at each location. If no FBA solution exists in the precomputed lookup table for a given set of parameters, the solution may be estimated by identifying one or more closest FBA solutions for the set of parameters and interpolating a solution from the one or more closest FBA solutions.

1.4.8. Regulation Module

In an embodiment, regulation module 326 updates the regulatory states of tissue(s) at one or more locations in the simulation volume of spatial model 302. Regulation module 326 may receive inputs from spatial model 302, chemical model 304, and/or tissue model 306, and update spatial model 302 based on these inputs. For example, regulation module 326 may receive local tissue densities and mechanical properties from spatial model 302, local chemical concentrations from chemical model 304, and/or one or more properties of tissue(s) from tissue model 306, and use this information to update the regulatory states of one or more tissues at one or more material points in the lattice of spatial model 302. Tissues in different regulatory states may be assigned different metabolism models, and may produce and/or consume different chemicals (e.g., nutrients, drugs, signaling molecules, etc.).

Cells mays change their regulatory states in response to their local environmental and biomechanical conditions. Thus, in an embodiment, regulation module 326 transitions tissues at each location within the simulation volume of spatial model 302 between regulatory states at rates that depend on the local concentrations of a predetermined number of chemicals (e.g., up to two, three, or more chemicals) or, potentially, all chemicals present at that location. These transitions may be accomplished in a similar manner as disclosed in Cole et al. However, the transition rates may take a wider range of functional forms than just the polynomial forms described in Cole et al. In addition, the set of properties that contribute to regulatory transitions may be expanded to include biomechanical cues (e.g., stresses, strains, etc.).

In an embodiment, spatial model 302 stores information on the current regulatory states of the tissues at each and every location in the simulation volume. This information may be represented, for each location i, as a set of values $\{\psi_{1,i}, \psi_{2,i}, \ldots, \psi_{N,i}\}$ that collectively describe the fraction of a given tissue in each of its N possible states at the location i. Tissue model 306 may comprise mathematical descriptions of how the tissues transition between these states as functions of various chemical and physical parameters. For example, if a given tissue can exist in either a normoxic or hypoxic state, then the fractions that exist in either state at location i may be represented as $\{\psi_{n,i}, \psi_{h,i}\}$, wherein the subscript n denotes the normoxic state, and the subscript h denotes the hypoxic state. Tissue model 306 may also specify the rates at which the tissue transitions between the normoxic and hypoxic states, depending on the local oxygen concentration $[O]_i$. This may be represented by the functions $k_{n \to h}([O]_i)$ and $k_{h \to n}([O]_i)$. At each time step $\Delta t$ of the simulation, the normoxic and hypoxic fractions in $\{\psi_{n,i}, \psi_{h,i}\}$ can be updated as follows:

$$\psi_{n,i} \leftarrow \psi_{n,i} - k_{n \to h}([O]_i) \cdot \psi_{n,i} \cdot \Delta t + k_{h \to n}([O]_i) \cdot \psi_{h,i} \cdot \Delta t$$

$$\psi_{h,i} \leftarrow \psi_{h,i} - k_{h \to n}([O]_i) \cdot \psi_{h,i} \cdot \Delta t + k_{n \to h}([O]_i) \cdot \psi_{n,i} \cdot \Delta t$$

1.4.9. Advection Module

In an embodiment, advection module 328 updates the chemical concentrations at one or more locations in spatial model 302, to reflect the effect of advection. Advection module 328 may receive inputs from spatial model 302, chemical model 304, and/or tissue model 306, and update spatial model 302 based on these inputs. For example, advection module 328 may receive spatial distributions of chemicals and tissues from spatial model 302, the properties of chemical(s) from chemical model 304, and/or the properties of tissue(s) from tissue model 306, and use this information to update the chemical concentrations at one or more locations in the simulation volume of spatial model 302.

In certain cases (e.g., when chemicals are bound or internalized by the tissues), chemicals may advect, along with the tissues, as they deform (e.g., as determined by mechanical module 330). In other cases, advection may occur within the vascular network to account for the flow of blood. In any case, the mathematical form of the continuity equation that governs the advection of a chemical, whose concentration is represented by $\varphi$ is given by $$\frac{\partial \varphi}{\partial t} = -\nabla \cdot (\varphi u),$$

wherein u represents the vector-valued flow field. This can be approximated in a straightforward manner on a lattice. For example, the concentration at a location, indexed in three dimensions by (i, j, k) can be updated as:

$$\varphi(i,j,k) \leftarrow \varphi(i,j,k) - \{[\varphi(i+1,j,k) \cdot u_x(i+1,j,k) - \varphi(i-1,j,k) \cdot u_x(i-1,j,k)] - [\varphi(i,j+1,k) \cdot u_y(i,j+1,k) - \varphi(i,j-1,k) \cdot u_y(i,j-1,k)] - [\varphi(i,j,k+1) \cdot u_z(i,j,k+1) - \varphi(i,j,k-1) \cdot u_z(i,j,k-1)]\} \cdot \Delta t / 2\lambda$$

wherein $\lambda$, represents the spacing of the lattice, and $u_x(i, j, k)$, $u_y(i, j, k)$, and $u_z(i, j, k)$ represent the components of the vector u at location (i, j, k).

1.4.10. Mechanical Module

In an embodiment, mechanical module 330 updates the locations, masses, volumes, and/or densities of tissue(s) within spatial model 302. Mechanical module 330 may receive inputs from spatial model 302 and/or tissue model 306, and update spatial model 302 based on these inputs. For example, mechanical module 330 may receive the current configuration of tissue(s) from spatial model 302 and/or one or more mechanical properties of tissue(s) from tissue model 306, and use this information to update the locations and/or densities of tissue(s) within spatial model 302.

Tissues can grow and shrink at different locations in response to the available concentrations of nutrients and/or drugs. As a result, the conformation of the tissues must change. In an embodiment, the tissues are described as elastic materials within the simulation. For example, mechanical module 330 may implement a mass spring model (MSM) in which the tissues are discretized to a network of points connected by representations of "springs." The stiffness of the springs on each tissue type can be changed to account for the differing stiffness of the tissue types.

After the tissue densities $\psi$, at each location i, are updated (e.g., by metabolism module 324), the lengths of the springs connected to the point(s) that fall within location i are modulated accordingly. For example, if $\psi_i$ was doubled, the lengths of the springs on the corresponding points would be scaled by $2^{1/3}$, such that the effective volume of the points in their unstressed conformations becomes twice what it was before. In addition, forces on each point may be computed according to the prescription described in Kot et al. or another similar scheme. These computed forces are then used to update the positions of the points. This may be done iteratively until the entire system of springs reaches equilibrium. Then, the final locations of the points (i.e., at equilibrium) are interpolated to a regular lattice in order to update the densities of the tissues at each location in the simulation volume of spatial model 302.

1.4.11. Cell Biochemistry Module

In an embodiment, cell biochemistry module 332 updates the chemical concentrations at one or more locations in the simulation volume of spatial model 302, to reflect non-metabolic chemical reactions carried out by tissue(s). Such chemical reactions may include, without limitation, the production of a diffusible signaling molecule, such as vascular endothelial growth factor (VEGF). Cell biochemistry module 332 may receive inputs from spatial model 302, chemical model 304, tissue model 306, and/or drug interaction model 308, and update spatial model 302 based on these inputs. For example, cell biochemistry module 332 may receive the density and regulatory state of tissue(s) at one or more locations from spatial model 302 and tissue model 306, one or more chemical properties of molecule(s) from chemical model 304, and/or drug impacts from drug interaction model 308, and use this information to update the chemical concentrations at one or more material points in the lattice of spatial model 302.

In an embodiment, the rate at which a given chemical reaction is carried out by the local tissues, at each location in the simulation volume of spatial model 302, is computed according to a functional form defined in tissue model 306. As a simple example, if such a reaction represented the production of a chemical at a constant rate k, by a tissue $\psi$, then the concentration of the chemical at location i can be updated as $\psi_i \leftarrow \psi_i + k \cdot \psi_i \cdot \Delta t$. Of course, it should be understood that the functional forms of the rates can be arbitrarily defined, and the reactions can involve more than one chemical.

1.4.12. Drug Interaction Module

In an embodiment, drug interaction module 334 updates the chemical concentrations and/or tissue densities at one or more locations in the simulation volume of spatial model 302, to reflect drug uptake, killing of local tissues, and/or the like. Drug interaction module 334 may receive inputs from spatial model 302, chemical model 304, tissue model 306, and/or drug interaction model 308, and update spatial model 302 based on these inputs. For example, drug interaction module 334 may receive the spatial distributions of drug(s) and/or tissue(s) from spatial model 302, one or more chemical properties of drug(s) from chemical model 304, behaviors of individual tissue(s) from tissue model 306, and/or drug impacts from drug interaction model 308, and use this information to update the chemical concentrations and/or tissue densities at one or more material points in the lattice of spatial model 302.

In an embodiment, drug interaction model 308 includes the rate at which the drugs in the simulation interact with and kill the tissues, and specifies what data is required to update the chemical concentrations and tissue densities accordingly. Drug interaction module 334 performs these updates.

Returning to the example of trastuzumab, the drug might bind and unbind cell surface receptors at rates $k_b$ and $k_u$, respectively. The concentration $\varphi_b$ of the bound drug and the concentration $\varphi_u$ of the unbound drug at each location i can then be updated as:

$$\varphi_{b,i} \leftarrow \varphi_{b,i} + k_b(\gamma\psi_i - \varphi_{b,i}) \cdot \varphi_{u,i} \cdot \Delta t - k_u \cdot \varphi_{b,i} \cdot \Delta t$$

$$\varphi_{u,i} \leftarrow \varphi_{u,i} - k_b(\gamma\psi_i - \varphi_{b,i}) \cdot \varphi_{u,i} \cdot \Delta t - k_u \cdot \varphi_{b,i} \cdot \Delta t$$

wherein $\gamma$ is a proportionality constant between tissue density $\psi_i$ and receptor concentration, such that $(\gamma\psi_i - \varphi_{b,i})$ represents the concentration of unbound receptors. Assuming that the tissue is subsequently killed by immune cells at some rate $k_{kill}(\varphi_{b,i})$ that is given as a function of the concentration of the bound drug, the local density of the tissue can be updated as:

$$\psi_i \leftarrow \psi_i - k_{kill}(\varphi_{b,i}) \cdot \tau_i \cdot \psi_i \cdot \Delta t$$

wherein $\tau_i$ represents the local density of immune effector cells.

For doxorubicin, the drug can be uptaken and effluxed by the tissues. As such, there may exist intracellular and extracellular versions of the drug's concentrations, $\varphi_{int}$ and $\varphi_{ext}$, respectively. The rates at which uptake and efflux can occur for a given tissue type may be defined in drug interaction model 308, as functions of the respective drug concentrations (e.g., $k_{uptake}(\varphi_{ext})$ and $k_{efflux}(\varphi_{int,i})$, respectively). Drug interaction module 334 may update the local concentrations at location i as:

$$\varphi_{ext,i} \leftarrow \varphi_{ext,i} + k_{efflux}(\varphi_{int,i}) \cdot \varphi_{int,i} \cdot \psi_i \cdot \Delta t - k_{uptake}(\varphi_{ext}) \cdot \psi_i \cdot \Delta t$$

$$\varphi_{int,i} \leftarrow \varphi_{int,i} - k_{efflux}(\varphi_{int,i}) \cdot \varphi_{int,i} \cdot \psi_i \cdot \Delta t + k_{uptake}(\varphi_{ext}) \cdot \varphi_{ext} \cdot \psi_i \cdot \Delta t$$

Within the simulation, the drug may kill the local tissues at some rate that is a function of both the intracellular concentration of the drug and the proliferation rate of the tissue, in order to account for the fact that doxorubicin is selective for proliferating cells. Drug interaction module 334 would then update the tissue density as:

$$\psi_i \leftarrow \psi_i - k_{kill}(\varphi_{int,i}, g_i) \cdot \Delta t$$

wherein $k_{kill}(\varphi_{int,i}, g_i)$ represents the killing rate of the tissue, and $g_i$ represents the local proliferation rate of the tissue (e.g., computed by metabolism module 324).

1.4.13. Immune System Module

In an embodiment, immune system module 336 updates the state of a simulated immune system response at one or more locations in the simulation volume of spatial model 302. Immune system module 336 may receive inputs from immune spatial model 302, chemical model 304, tissue model 306, drug interaction model 308, and/or immune system model 310, and update spatial model 302 based on these inputs. For example, immune system module 336 may receive the spatial distributions of immune-therapeutic drugs from spatial model 302 and/or drug interaction model 308, the spatial distributions of other chemical species from chemical model 304, and/or the state of local tissue(s) and/or mechanical cues from tissue model 306, and use this information to update the state of the simulated immune system response at one or more material points in the lattice of spatial model 302.

Immune cells may be represented as either discrete particles or a scalar field describing immune cell density, depending on the detail and overall scale of the simulation. In the event that the immune cells are represented as discrete particles, the probability of an immune cell particle at location i remaining at current location i or jumping to any one of its neighboring locations (i.e., adjacent to or otherwise neighboring location i) may be given by a set $\{P_{i \to j}\}$, where $i \in \{j\}$, normalized such that $\Sigma_j P_{i \to j} = 1$. Each probability may be a function of the local concentrations of different chemicals (e.g., chemo-attractants) or their gradients, as well as the local densities of the tissues. By generating a uniform pseudo-random number in the interval [0,1], immune system module 336 may select a jump of the immune cell from its current location i to one of its neighboring locations. In the event that the immune cells are represented by a scalar field T, the motion of the immune cells may be described as a mix of diffusion (e.g., defined by diffusion module 322) and advection (e.g., defined by advection module 328), with the latter representing chemotaxis along the concentration gradient of a chemo-attractant.

Immune cells may also undergo regulatory or phenotypic transitions between states, in response to local concentrations of chemicals and/or drugs and/or tissue densities. The regulatory states may represent active or inactive states of the tissue cells. For example, active immune cells may be deactivated by cancer cells expressing programmed death-ligand 1 (PD-L1). A PD-L1-targeted drug might bind the PD-L1, preventing deactivation of the immune cells, thereby enabling them to kill the cancer tissue. If the immune cells are represented as discrete particles, these transitions may be stochastic. The probability of each possible transition may be computed, and a random number may be generated to select which transition occurs for each immune cell. On the other hand, if the immune cells are represented by a scalar field, the transitions may be described in similar terms to that of the tissue regulatory transitions (e.g., described elsewhere herein with respect to regulation module 326).

2. Process Overview

Embodiments of processes for generating a three-dimensional model of a patient-specific tumor and simulating the patient-specific tumor's behavior over time will now be described in detail. It should be understood that the described processes may be embodied in one or more software modules that are executed by one or more hardware processors (e.g., processor 210), e.g., as the application discussed herein (e.g., server application 112, client application 132, and/or a distributed application comprising both server application 112 and client application 132), which may be executed wholly by processor(s) of platform 110, wholly by processor(s) of user system(s) 130, or may be distributed across platform 110 and user system(s) 130, such that some portions or modules of the application are executed by platform 110 and other portions or modules of the application are executed by user system(s) 130. The described process may be implemented as instructions represented in source code, object code, and/or machine code. These instructions may be executed directly by the hardware processor(s), or alternatively, may be executed by a virtual machine operating between the object code and the hardware processors. In addition, the disclosed application may be built upon or interfaced with one or more existing systems.

Alternatively, the described processes may be implemented as a hardware component (e.g., general-purpose processor, integrated circuit (IC), application-specific integrated circuit (ASIC), digital signal processor (DSP), field-programmable gate array (FPGA) or other programmable logic device, discrete gate or transistor logic, etc.), combination of hardware components, or combination of hardware and software components. To clearly illustrate the interchangeability of hardware and software, various illustrative components, blocks, modules, circuits, and steps are described herein generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a component, block, module, circuit, or step is for ease of description. Specific functions or steps can be moved from one component, block, module, circuit, or step to another without departing from the invention.

2.1. Overall Process

Figure 4:
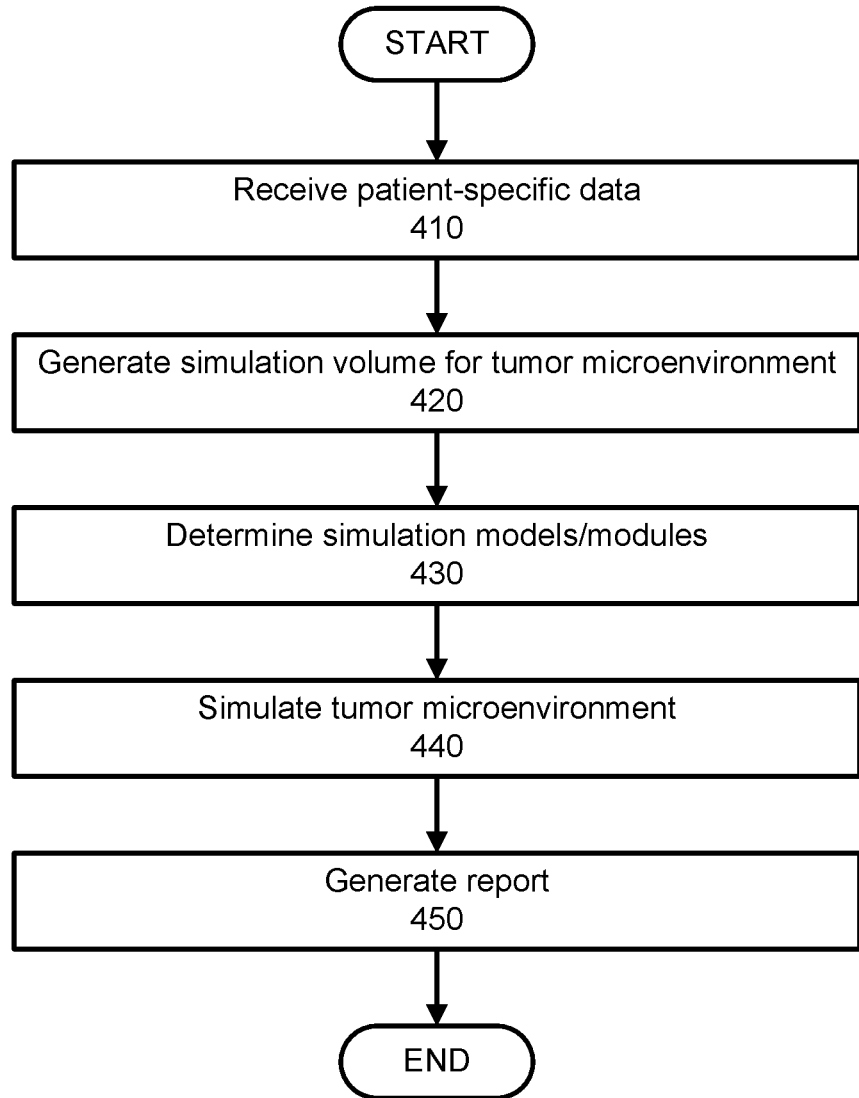
FIG. 4 is a flowchart that illustrates an overarching process for performing a simulation, according to an embodiment.

FIG. 4 is a flowchart that illustrates an overarching process for performing a simulation, according to an embodiment. While process 400 is illustrated with a certain arrangement and ordering of steps, process 400 may be implemented with fewer, more, or different steps and a different arrangement and/or ordering of steps. Process 400 may be implemented by server application 112, or by the combination of an external application with server application 112, as described elsewhere herein.

In a typical scenario, a simulation will be ordered by a user via graphical user interface 150. Specifically, the user (e.g., healthcare provider or other professional) may sign in to server application 112 and/or an external application (e.g., logically positioned in front of server application 112). Appropriate and well-known authentication and/or other security protocols may be used to ensure that only users with particular roles and/or permissions are permitted to sign in. Once signed in, the user may order a simulation via billing module 164. For example, graphical user interface 150 may provide the user with one or more inputs for ordering the simulation, specifying one or more drugs to be modeled and simulated, specifying dosages and schedules for the drug(s) (e.g., frequency and duration of administration), specifying a time duration to be simulated, and/or specifying any other user-definable parameters to be used by simulation engine 180.

The user may also input patient-specific data via graphical user interface 150. The data may be input in any well-known manner, and may comprise, automatically or with the user's input, retrieving at least a portion of the patient-specific data from an EMR of the patient using EMR module 162. For example, graphical user interface 150 may comprise one or more inputs for manually entering information (e.g., textbox, drop-down menus, checkboxes, and/or the like), one or more inputs for selecting a file to upload (e.g., a browse input that opens a file system window of a user system 130 that allows selection of a file from the file system), one or more inputs for retrieving information (e.g., from an EMR stored on platform 110 or one or more external systems 140), and/or the like. Alternatively or additionally, the patient-specific data may be communicated directly from an external system 140 to platform 110, without the need of graphical user interface 150, or using a graphical user interface of the external system 140.

Prior to step 410, the application (e.g., server application 112 and/or an external application) may perform "sanity" checks to ensure that the ordered simulation is possible and/or reasonable (e.g., the patient's EMR contains the necessary patient-specific data, the specified dosages and schedules comply with recommended ranges, other specified simulation parameters are reasonable, etc.), and/or provide additional tools (e.g., for interfacing with the patient's EMR). In addition, preprocessing module 160 may anonymize the patient-specific data (e.g., remove all patient-identifying information from the patient-specific data). If preprocessing module 160 is implemented by an external application, the external application may securely transfer the anonymized patient-specific data to server application 112, such that server application 112 receives the necessary patient-specific data without ever receiving any patient-identifying data.

In step 410, the application (e.g., server application 112) receives patient-specific data 172. As discussed above, patient-specific data 172 may have been previously scrubbed of any patient-identifying information. Patient-specific data 172 may comprise a plurality of data sets, including, without limitation, imaging data representing an image of the patient's tumor and surrounding tissues (i.e., the tumor microenvironment), genomics for the patient, gene expression profiling for the patient, histopathology data of the patient, blood work for the patient (e.g., including concentrations of metabolites, etc.), and/or the like. While not all of these data sets are essential, each is useful in various implementations of simulation engine 180. The imaging data may comprise magnetic resonance imaging (MRI) data, positron emission topography (PET) data, and/or computed tomography (CT) data.

In step 420, the application (e.g., server application 112) generates spatial model 302, comprising a three-dimensional simulation volume that represents the structure of tumor microenvironment. For example, spatial model generation module 174 may generate spatial model 302 based on the imaging (e.g., MRI, PET, CT, etc.) data within patient-specific data 172. As discussed elsewhere herein, the simulation volume of spatial model 302 may be a cubic lattice or other structured or unstructured lattice.

In step 430, the application (e.g., server application 112) determines the models and/or modules to be used to simulate the tumor microenvironment. In an embodiment, step 430 may comprise generating one or more patient-specific models and/or modules based on patient-specific data 172, or selecting one or more patient-appropriate models and/or modules from a plurality of available models and/or modules based on patient-specific data 172. For example, drug interaction model generation module 176 may generate a patient-specific drug interaction model 308, tissue model generation module 178 may generate or select a patient-specific metabolism model to be used by tissue model 306, and/or an immune system model creation module (not shown) may generate a patient-specific immune system model 310. More specifically, in an embodiment, drug interaction model generation module 176 may assign each tissue, to be represented in tissue model 306, its own drug interaction model 308, to describe how quickly it uptakes a given drug, how fast and at what concentrations the cells are killed by a given drug, and/or the like, based on the genomics for the patient, gene-expression profiling for the patient, and/or the histopathology data of the patient in patient-specific data 172. Similarly, tissue model generation module 178 may assign each tissue, to be represented in tissue model 306, its own model to describe its metabolism, based on the genomics for the patient, gene-expression profiling for the patient, and/or the histopathology data of the patient in patient-specific data 172.

In step 440, the application (e.g., server application 112) simulates the tumor microenvironment over a plurality of iterations. Each iteration represents a time interval (e.g., Δt), such that, collectively, the plurality of iterations represent a time period. Simulation engine 180 may simulate the tumor microenvironment over the time period for each of a plurality of drug interventions, as well as without any drug intervention (e.g., for comparison). The duration of the time period may be specified by the user (e.g., via graphical user interface 150 when specifying the patient-specific data and/or other request data), by an operator, or by a system setting.

In step 450, the application (e.g., server application 112) generates a report based on the result of the simulation performed in step 440. The report may comprise one or more screens, frames, or other regions in graphical user interface 150. For example, the report may comprise a navigable HTML document. The HTML document may comprise a plurality of webpages, including a first webpage that comprises important and easily digestible information (e.g., key statistics, such as the reduction in tumor volume for each drug intervention that was tested), and one or more additional webpages that comprise more comprehensive information, such as more detailed or granular statistics and/or a visual representation of the tumor or the tumor microenvironment. Alternatively or additionally, the report may comprise another type of electronic (e.g., PDF file) or non-electronic document (e.g., paper hardcopy) that is appropriate for a clinical setting.

In an embodiment, the report comprises one or more statistics. The reported statistics may include, without limitation, a predicted change in volume of the tumor for each drug intervention (e.g., chemotherapeutic agent) that is tested, a predicted change in volume of the tumor without any drug intervention, a measure of difference (e.g., percentile difference) between each predicted change in volume of the tumor and the change in tumor volume for other patients, estimates of tumor boundaries after each drug intervention and/or without drug intervention, penetration depth of each drug that is tested, average intra-tumoral drug concentration, average costs associated with each drug intervention (e.g., costs of each chemotherapeutic agent treatment regimen), other systemic risks associated with each drug intervention (e.g., infertility, immunosuppression, etc.), and/or the like. The report may also comprise error estimates associated with each statistic.

In an embodiment, the report comprises one or more two-dimensional and/or three-dimensional visual representations of the tumor microenvironment over time. For example, in an embodiment in which the report is provided within a graphical user interface, the report may comprise an interactive three-dimensional representation of the tumor microenvironment (i.e., the tumor and its surrounding tissues). The three-dimensional representation may be rotatable around one or a plurality of axes via one or more input operations (e.g., selection of input(s) in the graphical user interface, operation of a keyboard or pointing device, touch gestures for devices with touch sensors, etc.). The three-dimensional representation may also be scalable via one or more inputs (e.g., using a mouse wheel to increase or reduce magnification, using a pinch-in gesture to reduce magnification or "zoom out" and using a pinch-out gesture to increase magnification or "zoom in"). In addition, the three-dimensional representation may be advanced or reversed over the entire time period of the simulation. For example, the graphical user interface may comprise a slider input that can be moved in one direction (e.g., left) to show a three-dimensional representation of the tumor microenvironment at an earlier iteration of the simulation, and moved in the opposite direction (e.g., right) to show a three-dimensional representation of the tumor microenvironment at a later iteration of the simulation. It should be understood that inputs, other than a slider (e.g., left and right arrow buttons, etc.), may be used in a similar manner.

2.2. Generation of Simulation Volume

Figure 5:
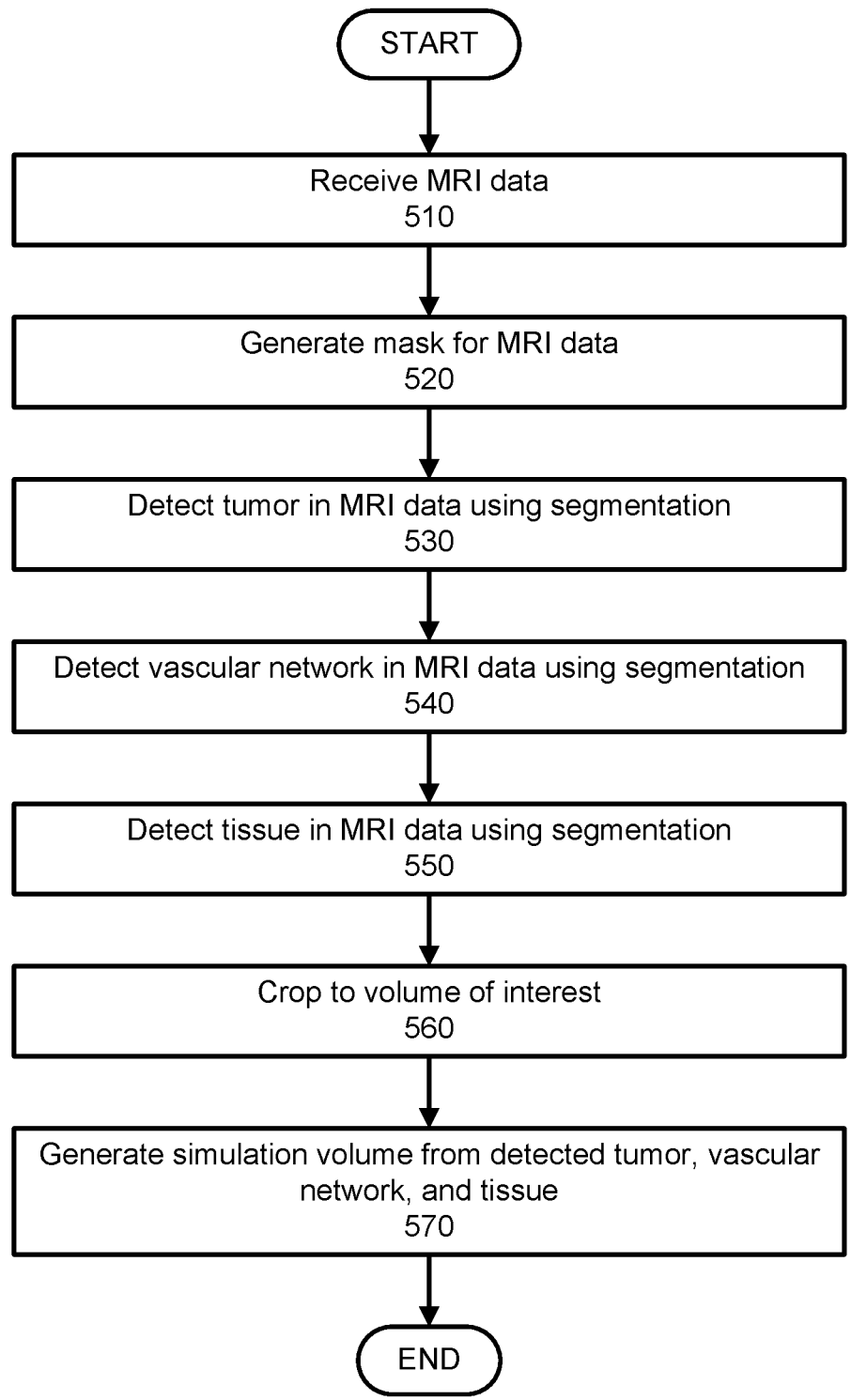
FIG. 5 is a flowchart that illustrates an example process for generating a simulation volume representing a patient-specific tumor microenvironment, according to an embodiment.

FIG. 5 is a flowchart that illustrates an example process 420 for generating a simulation volume representing a patient-specific tumor microenvironment, according to an embodiment. While process 420 is illustrated with a certain arrangement and ordering of steps, process 420 may be implemented with fewer, more, or different steps and a different arrangement and/or ordering of steps. Process 420 corresponds to step 420 in process 400, and may be implemented by server application 112. Specifically, process 420 may be implemented by spatial model generation module 174 to construct a three-dimensional simulation volume of a patient-specific tumor microenvironment from the imaging data within patient data 172.

In an embodiment, one or more steps of process 420 may be monitored by a user (e.g., via one or more screens of graphical user interface 150 generated by server application 112). The user may interact with each monitored step to perform certain tasks required by the step and/or confirm that the step was correctly performed before proceeding to a subsequent step. Alternatively, process 420 may be performed automatically by spatial model generation module 174 without any user monitoring and/or interaction, and, in an embodiment, without any user involvement whatsoever.

In step 510, spatial model generation module 174 receives imaging (e.g., MRI, PET, CT, etc.) data representing a three-dimensional image of the patient's tumor within its environment. The contrast in the imaging data may be dynamically enhanced to aid in subsequent steps (e.g., steps which perform segmentation).

In step 520, spatial model generation module 174 generates a mask for regions that should be ignored during subsequent steps. These regions to be ignored and for which the mask is generated may comprise regions of non-tissue, such as air, in the imaging data. The regions to be masked may comprise any pixels or pixel clusters with an intensity value below a minimum intensity threshold value. The minimum intensity threshold value may represent the lowest intensity value that would be expected for tissue, such that pixels or clusters above the minimum intensity threshold value are classified as tissue, and pixels or clusters below the minimum intensity threshold value are classified as non-tissue to be masked. It should be understood that pixels or clusters that are equal to the minimum intensity threshold can be classified as tissue or non-tissue based on the programmer's design choice. In an embodiment, the minimum intensity threshold value may be initially set to a default value, and subsequently adjusted should the need arise (e.g., by a user input). The need may arise, for example, if subsequent steps (e.g., steps 530-550) fail to properly detect the tumor, vascular network, and/or other tissues.

In step 530, spatial model generation module 174 detects tumor tissue within the unmasked regions of the imaging data. In an embodiment, spatial model generation module 174 uses segmentation to detect the tumor mass. For example, a blob-detection algorithm may be used. Within each slice of the three-dimensional imaging data and/or across slices of the three-dimensional imaging data, the algorithm may select one or more seed pixels (e.g., based on a threshold intensity value, which may, for example, be specified by a user, operator, or system setting), and then "grow" segments of pixels around these seed pixel(s) to create one or more clusters of pixels representing the tumor tissue. Suitable methods for identifying and/or segmenting tumor tissue are described in U.S. Pat. No. 7,317,821, issued on Jan. 8, 2008, and U.S. Pat. No. 7,466,848, issued on Dec. 16, 2008, which are hereby incorporated herein by reference as if set forth in full.

In step 540, spatial model generation module 174 detects the vascular network within the unmasked regions of the imaging data. In an embodiment, spatial model generation module 174 uses segmentation to segment blood vessels. For example, spatial model generation module 174 may apply standard filtering and de-noising operations to the unmasked imaging data, and select one or more seed pixels (e.g., based on a threshold intensity value, which may, for example, be specified by a user, operator, or system setting) from the filtered and de-noised imaging data. From each seed pixel, a directionality of blood vessels may be computed according to the eigenvectors of the Hessian matrix at each seed pixel. Segments of blood vessels are "grown" predominantly along the direction corresponding to the lowest eigenvalue. Suitable methods for identifying and/or segmenting a vascular network are described in U.S. Pat. No. 5,204,625, issued on Apr. 20, 1993, U.S. Patent Pub. Nos. 2010/0296709, published on Nov. 25, 2010, and 2011/0170759, published on Jul. 14, 2011, "Multi-Scale Blood Vessel Detection and Segmentation in Breast MRIs," by Kahala et al., Journal of Medical and Biological Engineering, pp. 1-7 (2018), and "A modified Seeded Region Growing algorithm for vessel segmentation in breast MRI images for investigating the nature of potential lesions," by Glotsos et al., Journal of Physics: Conference Series, 490:012136 (2014), which are all hereby incorporated herein by reference as if set forth in full.

In step 550, spatial model generation module 174 detects other tissue within the unmasked regions of the imaging data. In an embodiment, spatial model generation module 174 uses the same basic segmentation method, used to detect tumor tissue in step 530, to detect other tissue in step 550. The tissue may be classified (e.g., as either adipose or fibroglandular tissue in the case of a breast cancer tumor) using a Gaussian mixture model. For example, the distribution of pixel intensities in the imaging data may be fit by a sum of N Gaussian distributions (each representing one of N tissue types). Then, each pixel may be assigned to one of the Gaussian distributions based on its intensity value.

In step 560, spatial model generation module 174 crops the imaging data to consist of only a volume of interest. The volume of interest may consist of only the tumor, detected in step 530, and the portion of the vascular network and other tissues, detected in steps 540 and 550, respectively, that are immediately adjacent to the detected tumor. The volume of interest may be specified automatically or by a user, using depth, width, and height ranges.

In step 570, spatial model generation module 174 generates a simulation volume that represents the tumor detected in step 530, the vascular network detected in step 540, and the other tissues detected in step 550. In an embodiment, the entire tumor microenvironment, comprising the detected tumor, vascular network, and other tissues can be represented as a lattice (e.g., cubic lattice) comprising a plurality of connected lattice sites (also referred to herein as "material points").

Using breast cancer as an illustrative, non-limiting example, the simulation volume may include tumor tissue, adipose (fat) tissue, glandular tissue, and vascular tissue. Spatial model generation module 174 may mask regions in the imaging data that represent air (step 520), and then isolate the tumor tissue and vascular networks in the unmasked regions of the imaging data (steps 530 and 540). Next, spatial model generation module 174 may employ a Gaussian mixture model (GMM) to differentiate the adipose and glandular tissues in the unmasked regions of the imaging data (step 550). Then, spatial model generation module 174 may generate a volume representing the isolated tumor tissue, vascular networks, adipose tissue, and glandular tissue as a lattice, and crop that volume to just the region of imaging data that includes the tumor and its surrounding nearby tissues (steps 560 and 570). This final segmented and cropped volume represents the initial simulation volume of the tumor microenvironment to be input to simulation engine 180.

2.3. Generation of Drug Interaction Model

The application (e.g., server application 112) may construct a patient-specific drug interaction model 308 using the molecular and physiological tumor metrics that are most commonly available within patient data 172. For example, the most commonly available metrics for breast-cancer tumors include hormone receptor status, HER2 expression status, tumor type (e.g., adenocarcinoma, invasive ductal carcinoma, etc.), subtype (e.g., triple negative, luminal A or B, etc.), and certain key genomic signatures (e.g., BRCA1 and BRCA2 mutations, p53 mutations, etc.).

In an embodiment, the application leverages these tumor metrics along with drug sensitivity data for the drugs to be used in the simulation, in order to estimate each patient-specific tumor's sensitivity to each drug. Drug sensitivity data may be found, for example, in The Genomics of Drug Sensitivity in Cancer (GDSC) database. See, e.g., "Genomics of Drug Sensitivity in Cancer (GDSC): a resource for therapeutic biomarker discovery in cancer cells," by Yang et al., Nucleic Acids Research, 41(D1):D955-D961 (2012), which is hereby incorporated herein by reference as if set forth in full. With respect to breast cancer, the GDSC discloses drug sensitivity data for over two-hundred drugs in over forty breast cancer cell lines.

In an embodiment, the application (e.g., server application 112) searches for the combination of metrics which most effectively differentiate groups of cell lines by their sensitivities to a drug, for example, as measured by a silhouette coefficient. As a concrete example, consider a simple case in which only the estrogen receptor (ER) and progesterone receptor (PR) statuses are known for each patient. Three strategies exist to group the cell lines for which there is drug sensitivity data: by ER status alone, by PR status alone, or by both ER status and PR status. For each of these three grouping strategies, a silhouette coefficient can be computed. The grouping strategy with the highest silhouette coefficient represents the grouping strategy that best separates the cell lines of patients based on the cell lines' sensitivities to a given drug. The application can then estimate each cell line's sensitivity to the drug as the mean of the group that the cell line belongs to under the best grouping strategy.

During the three-dimensional simulation, drugs diffuse from the vasculature into the tumor microenvironment where they can be taken up by the local tissue cells. This leads to gradients in drug concentrations. Tissue cells near the blood vessels see higher drug concentrations and are killed quickly, while tissue cells farther from the blood vessels see lower drug concentrations and may not be killed at all. In an embodiment, a half maximal inhibitory concentration (IC50) value is used to parameterize the fraction of tissue cells that are killed by a drug at each location. Unfortunately, patients' sensitivities to different drugs differ, and, as a result, their effective IC50 values can be highly variable. Iorio et al. showed that that gene expression profiling was one of the best ways to predict the sensitivity of cancer cell lines to different drugs, followed by the cell lines' tissue of origin. While full transcriptomic or proteomic workups remain rare in the clinical setting, the application can leverage as much EMR data as possible, in order to predict drug sensitivity for each patient. For example, the GDSC includes IC50 values for hundreds of small-molecule drugs against thousands of cancer cell lines. By first selecting only GDSC data associated with the tissue of interest (e.g., breast, lung, etc.), the application can train a machine-learning algorithm (e.g., a multi-layer perceptron regressor) on variables that are commonly found in patients' EMRs. Such variables may include, for example, BRCA1 and BRCA2 mutation status, tumor protein p53 (TP53) mutation status, K167, HER2, estrogen and progesterone receptor expression levels, tumor type (e.g., invasive ductal carcinoma, adenocarcinoma, etc.), tumor subtype (e.g., basal, luminal, triple negative, etc.), demographic data (e.g., age, race, etc.), and/or the like. Based on each patient's EMR, the application may estimate the IC50 of the patient's cancer cells to different drugs. The application can then use these estimated IC50 values as parameters in a patient-specific drug interaction model 308. For instance, as described elsewhere herein, the killing rate of doxorubicin for a given patient's tumor may be assumed to be proportional to $1-(1+\varphi_{int}/IC50)^{-1}$, wherein $\varphi_{int}$ represents the intracellular concentration of the drug.

Alternatively, the application may utilize more advanced machine-learning approaches, such as logic regression or random forest regression, which may be of greater utility as comprehensive gene-expression profiling becomes more common. Examples of such machine-learning approaches are described in "Logic Regression," by Ruczinski et al., Journal of Computational and Graphical Statistics, 12(3): 475-511 (2003), and "Classification and Regression by Random Forest," by Liaw et al., R News, 2(3):18-22 (2002), which are both hereby incorporated herein by reference as if set forth in full.

2.4. Generation of Metabolism Model

As discussed elsewhere herein, tissue model 306 may implement a metabolism model (e.g., for each tissue type). A completely personalized metabolism model (e.g., FBA) could be constructed for each patient to be used as the patient-specific metabolism model during simulation. However, rarely is there sufficient patient data to construct such a model. Thus, in an embodiment, an appropriate metabolism model is selected for a patient from a plurality of predefined metabolism models (e.g., stored in database(s) 114), based on the patient's patient data 172.

Specifically, the single most appropriate metabolism model to represent a patient's metabolism can be selected from among a set of models using the same type of molecular and physiological measures employed for estimating drug sensitivity. For example, over twelve-hundred breast-tumor-specific metabolism models have been constructed based on publicly available gene-expression datasets. To aid in the search and selection process, the predefined FBA models may be clustered using any suitable clustering algorithm, which may be tuned to produce fewer but larger clusters (e.g., for faster searching) or more but smaller clusters (e.g., for more accurate matching). For example, the breast-tumor-specific metabolism models were clustered into thirteen clusters. Each cluster may be represented by the metabolism model that is nearest the cluster's centroid (i.e., the cluster's archetype). The application (e.g., server application 112) may use a suitable classifier algorithm (e.g., a random forest classifier) to match a patient's patient data 172 (e.g., representing a set of clinical data) to the most representative archetype, and then select a metabolism model within the matching archetype's cluster based on a similarity to the patient data 172.

2.5. Simulation

In an embodiment, simulation engine 180 essentially couples a reaction-diffusion simulation with a simplified elastic material mechanical model of biological tissues. It simulates the transport of chemicals (e.g., nutrients and drugs) from the blood into the surrounding healthy and diseased tissues. It also simulates the uptake and metabolism of those chemicals by the tissues. For example, nutrients and drugs can be internalized either passively or actively, and nutrients can be metabolized by the cells in order to survive and grow, producing metabolic waste in the process.

Figure 6:
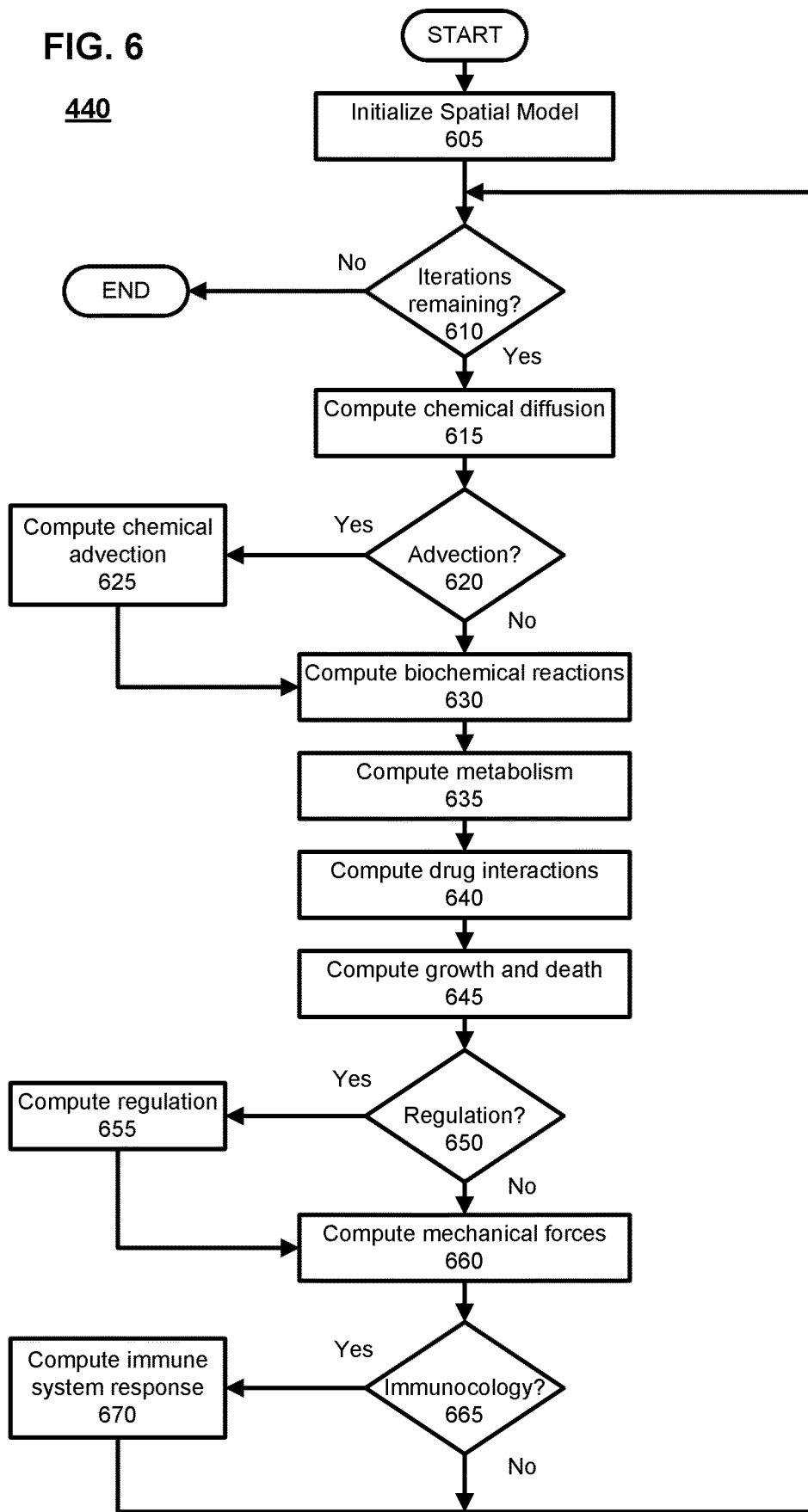
FIG. 6 is a flowchart that illustrates an example process for simulating a patient-specific tumor microenvironment, according to an embodiment.

FIG. 6 is a flowchart that illustrates an example process 440 for simulating a patient-specific tumor microenvironment, according to an embodiment. While process 440 is illustrated with a certain arrangement and ordering of steps, process 440 may be implemented with fewer, more, or different steps and a different arrangement and/or ordering of steps. Process 440 corresponds to step 440 in process 400, and may be implemented by simulation engine 180 of server application 112.

In step 605, simulation engine 180 initializes spatial model 302. For example, simulation engine 180 initializes all of the models and modules managed for a patient-specific tumor microenvironment (e.g., to reflect default and/or initial values and/or states). Then, simulation engine 180 advances spatial model 302 through a plurality of iterations. Each iteration represents a time interval and comprises at least a subset of steps 615-670. It should be noted that not all of steps 615-670 are necessarily executed in each iteration. The number of iterations for a given simulation may be a user-specified setting or system-wide setting. Alternatively, simulation engine 180 may continue executing iterations until the simulation is stopped by a user.

In step 610, if no iterations remain to be executed (i.e., "No" in step 610), simulation engine 180 will stop or pause the simulation. Otherwise, if iterations remain to be executed (i.e., "Yes" in step 610), simulation engine 180 proceeds to execute a new iteration of steps 615-670. In an embodiment in which simulation engine 180 advances the simulation through a predefined number of iterations, step 610 will determine that no iterations remain to be executed, as soon as the predefined number of iterations have been executed. In an embodiment in which simulation engine 180 advances the simulation until stopped (e.g., by a user operation), step 610 will determine that no iterations remain to be executed as soon as the simulation is stopped.

In step 615, simulation engine 180 computes the chemical diffusion for the current iteration. Specifically, diffusion module 322 may receive inputs from spatial model 302, chemical model 304, and tissue model 306, use those inputs to compute chemical diffusion within the tissues at each material point in the lattice of spatial model 302, and update spatial model 302 in accordance with the computation.

In an embodiment, simulation engine 180 may compute the chemical diffusion using a finite difference approximation on the lattice of the simulation volume of spatial model 302. For example, the differences may be computed between the concentration of a chemical at a location i and the concentrations of the same chemical at neighboring locations {j}. The number of neighboring locations to be used can be selected based on the design goals of the particular implementation. For example, for a cubic lattice, using the six nearest neighbors (e.g., forward, backward, up, down, left, and right of the location i) results in a "seven-point" method, whereas using a combination of the six nearest, twelve second nearest, and eight third nearest neighbors results in a "twenty-seven-point" method. While computationally more expensive than the seven-point method, the twenty-seven-point method is more numerically stable, enables longer time steps, and reduces the total number of diffusion operations. The optimal choice of method depends on the specifics of the overall algorithm. In the simplest case, when the diffusion coefficient D of a chemical is constant throughout a simulation volume, the concentration of the chemical at location i can be updated, using the seven-point method, as follows:

$$\varphi_i \leftarrow \varphi_i + D \cdot [(\Sigma_j \varphi_j) - 6\varphi_i] \cdot \Delta t / \lambda_2$$

In step 620, simulation engine 180 determines whether advection is applicable to the current iteration. If advection is applicable (i.e., "Yes" in step 620), simulation engine 180 computes chemical advection in step 625. Specifically, advection module 328 may receive inputs from spatial model 302, chemical model 304, and tissue model 306, use those inputs to compute chemical advection at each material point in the lattice of spatial model 302, and update spatial model 302 in accordance with the computation. Otherwise, if advection is not applicable (i.e., "No" in step 620), simulation engine 180 proceeds to the next step without executing step 625. In an embodiment, the user may specify the chemical concentrations that should be subject to advection (e.g., via one or more inputs of a graphical user interface of the application), which may depend on the details of the specific simulation being performed. Reasonable choices may include, for example, intracellular or cell-surface-bound drugs, chemicals within the blood vessels, and/or the like.

In step 630, simulation engine 180 computes the biochemical reactions for the current iteration. Specifically, cell biochemistry module 332 may receive inputs from spatial model 302, chemical model 403, and drug interaction model 308, use those inputs to compute biochemical reactions within the tissues at each material point in the lattice of spatial model 302, and update spatial model 302 in accordance with the computation.

In step 635, simulation engine 180 computes the metabolism for the current iteration. Specifically, metabolism module 324 may receive inputs from spatial model 302, chemical model 304, and the metabolism model of tissue model 306, use those inputs to compute the metabolism of the tissues at each material point in the lattice of spatial model 302, and update spatial model 302 in accordance with the computation.

In step 640, simulation engine 180 computes the drug interactions for the current iteration. Specifically, drug interaction module 334 may receive inputs from spatial model 302, chemical model 304, tissue model 306, and drug interaction model 308, use those inputs to compute the drug interactions within the tissues at each material point in the lattice of spatial model 302, and update spatial model 302 in accordance with the computation.

In step 645, simulation engine 180 computes the growth and death of tissues for the current iteration. Specifically, mechanical module 330 may receive inputs from spatial model 302 and tissue model 306, use those inputs to compute the growth and death of the tissues at each material point in the lattice of spatial model 302, and update spatial model 302 in accordance with the computation. The growth of tissues may be updated by metabolism module 324 and the death of tissues may be updated by drug interaction module 334. For example, metabolism module 324 may receive inputs from spatial model 302, tissue model 306, and drug interaction model 308, compute the growth of tissue at one or more locations (e.g., each and every location), and update spatial model 302 (e.g., update the tissue densities at the one or more locations) in accordance with these computations. Similarly, drug interaction module 334 may receive inputs from spatial model 302, tissue model 306, and drug interaction model 308, compute the death of tissue at one or more locations (e.g., each and every location), and update spatial model 302 (e.g., update the tissue densities at the one or more locations) in accordance with these computations.

In step 650, simulation engine 180 determines whether regulation is applicable to the current iteration. If regulation is applicable (i.e., "Yes" in step 650), simulation engine 180 computes regulation in step 655. Specifically, regulation module 326 may receive inputs from spatial model 302, chemical model 304, and tissue model 306, use those inputs to compute a regulatory state of the tissues at each material point in the lattice of spatial model 302, and update spatial model 302 in accordance with the computation. Otherwise, if regulation is not applicable (i.e., "No" in step 650), simulation engine 180 proceeds to the next step without executing step 655. In an embodiment, the regulation computations are determined to be applicable (i.e., "Yes" in step 650) based on data in tissue model 306. For example, if one or more tissues can exist in multiple regulatory states and transition rate models are defined for the tissue(s) (e.g., in tissue model 306), then regulation may be determined to be applicable (i.e., "Yes" in step 650), thereby triggering regulation module 326 to compute the regulation for each of the tissue(s) in step 655.

In step 660, simulation engine 180 computes the mechanical forces for the current iteration. Specifically, mechanical module 330 may receive inputs from spatial model 302 and tissue model 306, use those inputs to compute the mechanical forces at each material point in the lattice of spatial model 302, and update spatial model 302 in accordance with the computation.

In step 665, simulation engine 180 determines whether immunocology is applicable to the current iteration. If immunocology is applicable (i.e., "Yes" in step 665), simulation engine 180 computes immune system response in step 670. Specifically, immune system module 336 may receive inputs from chemical model 304, tissue model 306, drug interaction model 308, and immune system model 310, use those inputs to compute an immune system response at each material point in the lattice of spatial model 302, and update spatial model 302 in accordance with the computation. Otherwise, if immunocology is not applicable (i.e., "No" in step 665), simulation engine 180 proceeds to the next step without executing step 670. Whether or not immunocology is applicable may be depend on the simulation inputs. For example, some drugs (e.g., trastuzumab, immune checkpoint inhibitors, etc.) are dependent on the immune system for their modes of action. When such drugs are being simulated by simulation engine 180, simulation engine 180 may determine that immunocology is applicable (i.e., "Yes" in step 665), thereby triggering immune system module 336 to compute the immune system response to each of these drug(s) in step 670. Alternatively, in an embodiment which does not utilize immune system model 310 and/or immune system module 336, steps 665 and 670 may be omitted.

The above description of the disclosed embodiments is provided to enable any person skilled in the art to make or use the invention. Various modifications to these embodiments will be readily apparent to those skilled in the art, and the general principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

Combinations, described herein, such as "at least one of A, B, or C," "one or more of A, B, or C," "at least one of A, B, and C," "one or more of A, B, and C," and "A, B, C, or any combination thereof" include any combination of A, B, and/or C, and may include multiples of A, multiples of B, or multiples of C. Specifically, combinations such as "at least one of A, B, or C," "one or more of A, B, or C," "at least one of A, B, and C," "one or more of A, B, and C," and "A, B, C, or any combination thereof" may be A only, B only, C only, A and B, A and C, B and C, or A and B and C, and any such combination may contain one or more members of its constituents A, B, and/or C. For example, a combination of A and B may comprise one A and multiple B's, multiple A's and one B, or multiple A's and multiple B's.

What is claimed is:

1. A method comprising using at least one hardware processor to:
    receive patient data for a patient, wherein the patient data comprises magnetic resonance imaging (MRI) data of a tumor microenvironment within the patient and one or more metrics of the patient;
    generate a patient-specific spatial model, comprising a representation of the tumor microenvironment as a three-dimensional lattice, from the MRI data within the patient data, wherein the three-dimensional lattice comprises a plurality of elastic-material points representing tissue within the tumor microenvironment;
    determine a patient-specific drug interaction model based on the one or more metrics within the patient data;
    determine a patient-specific metabolism model based on the one or more metrics within the patient data;
    for each of one or more drug interventions, simulate the tumor microenvironment by, for each of a plurality of iterations representing time intervals, for each of the plurality of elastic-material points,
        modeling chemical diffusion within the tissue represented by the elastic-material point and updating one or more properties of the elastic-material point based on the modeling of chemical diffusion,
        modeling one or more biochemical reactions within the tissue represented by the elastic-material point and updating one or more properties of the elastic-material point based on the modeling of the one or more biochemical reactions,
        modeling a metabolism of the tissue represented by the elastic-material point using the patient-specific metabolism model and updating one or more properties of the elastic-material point based on the modeling of metabolism,
        modeling one or more drug interactions with the tissue represented by the elastic-material point using the patient-specific drug interaction model and updating one or more properties of the elastic-material point based on the modeling of the one or more drug interactions,
        modeling one or both of growth and death of the tissue represented by the elastic-material point and updating one or more properties of the elastic-material point based on the modeling of one or both of growth and death,
        modeling mechanical forces at the elastic-material point and updating one or more properties of the elastic-material point based on the modeling of mechanical forces,
        modeling chemical advection within the tissue represented by the elastic-material point and updating one or more properties of the elastic-material point based on the modeling of chemical advection, wherein modeling chemical advection within the tissue represented by the elastic-material point and updating one or more properties of the elastic-material point based on the modeling of chemical advection comprises, for each of one or more chemicals, updating a concentration of the chemical at the elastic-material point (i, j, k) as:

$$\varphi(i, j, k) \leftarrow \varphi(i, j, k) -$$
$$\{[\varphi(i+1, j, k) \cdot u_x(i+1, j, k) - \varphi(i-1, j, k) \cdot u_x(i-1, j, k)] -$$
$$[\varphi(i, j+1, k) \cdot u_y(i, j+1, k) - \varphi(i, j-1, k) \cdot u_y(i, j-1, k)] -$$
$$[\varphi(i, j, k+1) \cdot u_z(i, j, k+1) - \varphi(i, j, k-1) \cdot u_z(i, j, k-1)]\} \cdot \frac{\Delta t}{2\lambda};$$

wherein $\varphi$ is a concentration of the chemical at the elastic-material point, $\lambda$ is a lattice spacing between elastic-material points in the lattice, and $u_x(i, j, k)$, $u_y(i, j, k)$, and $u_z(i, j, k)$ are components of a vector-valued flow field u at the elastic-material point,
        modeling at least one property of regulation within the tissue represented by the elastic-material point and updating one or more properties of the elastic-material point based on the modeling of regulation, and
        modeling at least one property of an immune system response within the tissue represented by the elastic-material point and updating one or more properties of the elastic-material point based on the modeling of the immune system response; and
    generate a report for at least one of the one or more drug interventions, wherein the report comprises a graphical user interface that comprises a three-dimensional visual representation of the patient-specific spatial model after one or more of the plurality of iterations, wherein the three-dimensional visual representation indicates one or more properties of at least a subset of the plurality of elastic-material points.

2. The method of claim 1, wherein modeling an immune system response within the tissue represented by the elastic-material point comprises modeling immune cells as discrete motile agents.

3. The method of claim 1, wherein modeling an immune system response within the tissue represented by the elastic-material point comprises modeling immune cells as a scalar field that describes immune cell density.

4. The method of claim 1, wherein modeling regulation within the tissue represented by the elastic-material point and updating one or more properties of the elastic-material point based on the modeling of regulation comprises:
receiving a current concentration of each of one or more chemicals at the elastic-material point;
receiving a current density and one or more mechanical properties of each of one or more types of tissue at the elastic-material point; and
for each of the one or more types of tissue at the elastic-material point,
determining a regulatory state, and
updating a regulatory state stored for the type of tissue to the determined regulatory state.

5. The method of claim 4, wherein each regulatory state is one of a plurality of possible regulatory states, wherein each of the plurality of possible regulatory states is associated with a different one of a plurality of metabolism models, and wherein modeling a metabolism of the tissue represented by the elastic-material point comprises, for each of the one or more types of tissue at the elastic-material point, using the metabolism model associated with the regulatory state stored for the type of tissue.

6. The method of claim 4, wherein the regulatory state of each of the one or more tissues is represented as a set of values that collectively describe a fraction of the tissue that is in each possible regulatory state.

7. The method of claim 1, wherein each of the plurality of elastic-material points is associated with a plurality of properties, wherein the plurality of properties comprise one or more chemical properties and one or more tissue properties.

8. The method of claim 7, wherein the one or more chemical properties comprise a chemical concentration for at least one chemical.

9. The method of claim 7, wherein the one or more tissue properties comprise a density of the tissue represented by the elastic-material point.

10. The method of claim 7, wherein the one or more tissue properties comprise a permeability of the tissue represented by the elastic-material point.

11. The method of claim 7, wherein the one or more tissue properties comprise a regulatory state of the tissue represented by the elastic-material point.

12. The method of claim 7, wherein modeling chemical diffusion within the tissue represented by the elastic-material point and updating one or more properties of the elastic-material point based on the modeling of chemical diffusion comprises:
receiving a current concentration, diffusion rate, and boundary value for each of at least one chemical at the elastic-material point;
receiving a current density of each of one or more types of tissue at the elastic-material point;
computing a new concentration for each of the at least one chemical and a new density of each of the one or more types of tissue, based on the current concentration, diffusion rate, and boundary value for the at least one chemical and the current density of the one or more types of tissue;
for each of the at least one chemical, updating the concentration of the chemical at the elastic-material point to the new concentration; and,
for each of the one or more types of tissue, updating the density of the type of tissue at the elastic-material point to the new density.

13. The method of claim 1, wherein the patient-specific spatial model is a spring model, such that each of the plurality of elastic-material points in the three-dimensional lattice is connected to each adjacent elastic-material point by a spring representation comprising a length value and a stiffness value.

14. The method of claim 13, wherein different tissue types are represented at the plurality of elastic-material points by different stiffness values.

15. The method of claim 13, wherein updating one or more properties of the elastic-material point based on the modeled mechanical forces comprises updating one or both of the length value and stiffness value of the spring representation between the elastic-material point and each adjacent elastic-material point.

16. The method of claim 15, wherein updating one or more properties of the elastic-material point based on the modeled mechanical forces comprises, until the mechanical forces reach an equilibrium:
updating the length value of the spring representation between the elastic-material point and each adjacent elastic-material point based on the mechanical forces; and
re-modeling the mechanical forces at the elastic-material point.

17. The method of claim 13, wherein each of the plurality of elastic-material points is associated with a plurality of properties, and wherein, for each of the one or more drug interventions, simulating the tumor microenvironment further comprises, at one or more times during the simulation, re-gridding the three-dimensional lattice of the spatial model, such that each of the plurality of elastic-material points maintains its plurality of properties but all of the spring representations between pairs of elastic-material points have equal length values.

18. The method of claim 1, further comprising using the at least one hardware processor to simulate the tumor microenvironment without any drug intervention, wherein the graphical user interface comprises a representation of a difference between the simulated tumor microenvironment with the at least one drug intervention and the simulated tumor microenvironment without any drug intervention.

19. The method of claim 1, wherein determining the patient-specific metabolism model comprises selecting the patient-specific metabolism model from a plurality of available metabolism models based on the one or more metrics within the patient data.

20. The method of claim 1, wherein the patient-specific metabolism model comprises a flux balance analysis (FBA) model.

21. The method of claim 1, wherein the tumor microenvironment comprises a tumor and tissues surrounding the tumor.

22. The method of claim 1, wherein the graphical user interface comprises:
a plurality of three-dimensional visual representations of the patient-specific spatial model at each of two or more of the plurality of iterations; and
one or more inputs for navigating between the plurality of three-dimensional visual representations in a chronological order represented by the two or more iterations.

23. The method of claim 1, wherein the three-dimensional lattice comprises a cubic lattice.

24. The method of claim 1, wherein modeling the metabolism of the tissue represented by the elastic-material point comprises:
based on one or more parameters, performing a lookup in a precomputed table of solutions derived from a flux balance analysis (FBA) model of chemical uptake; and, when a solution does not exist in the precomputed table for the one or more parameters, interpolating a solution from one or more solutions that do exist in the precomputed table.

25. The method of claim 1, wherein modeling one or more drug interactions with the tissue represented by the elastic-material point comprises computing at least one property of drug-related kinetics at the elastic-material point for each of one or more drugs modeled by the patient-specific drug interaction model.

26. The method of claim 25, wherein the patient-specific drug interaction model comprises a model of kinetic binding and unbinding rates for at least one drug.

27. The method of claim 25, wherein the patient-specific drug interaction model comprises a model of uptake and efflux of at least one drug by one or more tissue types.

28. The method of claim 1, wherein modeling a metabolism of the tissue represented by the elastic-material point and updating one or more properties of the elastic-material point based on the modeling of metabolism comprises:
receiving one or more properties of each of one or more chemicals at the elastic-material point, wherein the one or more properties comprise a current concentration;
modeling a metabolism of each of one or more types of tissue at the elastic-material point;
computing a new concentration for each of the one or more chemicals and a growth rate for each of the one or more types of tissue, based on the one or more properties of the one or more chemicals and the modeled metabolism of the one or more types of tissue;
for each of the one or more chemicals, updating the concentration of the chemical at the elastic-material point to the new concentration; and,
for each of the one or more types of tissue, updating a growth rate for the type of tissue to the new growth rate.

29. The method of claim 1, wherein modeling one or more biochemical reactions within the tissue represented by the elastic-material point and updating one or more properties of the elastic-material point based on the modeling of the one or more biochemical reactions comprises:
receiving one or more properties of each of one or more chemicals at the elastic-material point;
receiving a density and regulatory state for each of one or more types of tissue at the elastic-material point;
determining drug impacts using the patient-specific drug interaction model; and
updating concentrations of the one or more chemicals at the elastic-material point based on the one or more properties of the one or more chemicals, the density and regulatory state of the one or more types of tissue, and the drug impacts.

30. The method of claim 1, wherein modeling one or more drug interactions with the tissue represented by the elastic-material point using the patient-specific drug interaction model and updating one or more properties of the elastic-material point based on the modeling of the one or more drug interactions comprises:
receiving one or more properties of each of one or more drugs at the elastic-material point;
receiving a current density and determining a behavior for each of one or more types of tissue at the elastic-material point;
determining drug impacts of the one or more drugs using the patient-specific drug interaction model; and
updating densities of the one or more types of tissue at the elastic-material point based on the one or more properties of the one or more drugs, the current density and behavior of the one or more types of tissue, and the drug impacts.

31. The method of claim 1, wherein the patient-specific drug interaction model identifies a rate, per simulated time, at which one or more drugs kill one or more types of tissue.

32. A system comprising:
at least one hardware processor; and
one or more software modules that are configured to perform the method of claim 1 when executed by the at least one hardware processor.

33. A non-transitory computer-readable medium having instructions stored therein, wherein the instructions are configured to perform the method of claim 1 when executed by a processor.

34. A method comprising using at least one hardware processor to:
receive patient data for a patient, wherein the patient data comprises magnetic resonance imaging (MRI) data of a tumor microenvironment within the patient and one or more metrics of the patient;
generate a patient-specific spatial model, comprising a representation of the tumor microenvironment as a three-dimensional lattice, from the MRI data within the patient data, wherein the three-dimensional lattice comprises a plurality of elastic-material points representing tissue within the tumor microenvironment;
determine a patient-specific drug interaction model based on the one or more metrics within the patient data;
determine a patient-specific metabolism model based on the one or more metrics within the patient data;
for each of one or more drug interventions, simulate the tumor microenvironment by, for each of a plurality of iterations representing time intervals, for each of the plurality of elastic-material points,
modeling chemical diffusion within the tissue represented by the elastic-material point and updating one or more properties of the elastic-material point based on the modeling of chemical diffusion, wherein modeling chemical diffusion within the tissue represented by the elastic-material point x comprises, for each of one or more chemicals, modeling a chemical reaction as:

$$\varphi_{ext}(x, t + \Delta t) = \varphi_{ext}(x, t) - k(x, t)\Delta t;$$

$$\varphi_f(x, t + \Delta t) = \varphi_f(x, t) - k(x, t)\Delta t; \text{ and}$$

$$k(x, t) = \rho(x, t)\frac{Ek_{cat}}{V_{cell}}\frac{\varphi_{ext}(x, t)}{k_m + \varphi_{ext}(x, t)};$$

wherein $\varphi_{ext}(x, t)$ is an instantaneous local concentration of an extracellular form of the chemical at simulation time t, $\varphi_f(x, t)$ is an instantaneous local concentration of an intracellular form of the chemical at simulation time t, $\Delta t$ is the time interval represented by each of the plurality of iterations, $k(x, t)$ represents an instantaneous local uptake rate of the chemical in the tissue at simulation time t, $\rho(x, t)$ represents an instantaneous local cell volume fraction of the tissue at simulation time t, E represents a number of enzymatic transporters on a cell membrane of the tissue, $V_{cell}$ represents a volume of a cell of the tissue, $k_{cat}$ represents an enzyme turnover rate, and $k_m$ is a Michaelis constant for the chemical reaction, modeling one or more biochemical reactions within the tissue represented by the elastic-material point and updating one or more properties of the elastic-material point based on the modeling of the one or more biochemical reactions, modeling a metabolism of the tissue represented by the elastic-material point using the patient-specific metabolism model and updating one or more properties of the elastic-material point based on the modeling of metabolism, modeling one or more drug interactions with the tissue represented by the elastic-material point using the patient-specific drug interaction model and updating one or more properties of the elastic-material point based on the modeling of the one or more drug interactions, modeling one or both of growth and death of the tissue represented by the elastic-material point and updating one or more properties of the elastic-material point based on the modeling of one or both of growth and death, and modeling mechanical forces at the elastic-material point and updating one or more properties of the elastic-material point based on the modeling of mechanical forces; and generate and output a report for at least one of the one or more drug interventions, wherein the report comprises a graphical user interface that comprises a three-dimensional visual representation of the patient-specific spatial model after one or more of the plurality of iterations, wherein the three-dimensional visual representation indicates one or more properties of at least a subset of the plurality of elastic-material points.

35. The method of claim 34, wherein simulating the tumor microenvironment further comprises, for two or more of the plurality of iterations, for each of the plurality of elastic-material points:

modeling chemical advection within the tissue represented by the elastic-material point and updating one or more properties of the elastic-material point based on the modeling of chemical advection;

modeling regulation within the tissue represented by the elastic-material point and updating one or more properties of the elastic-material point based on the modeling of regulation; and modeling an immune system response within the tissue represented by the elastic-material point and updating one or more properties of the elastic-material point based on the modeling of the immune system response.

36. A method comprising using at least one hardware processor to:

receive patient data for a patient, wherein the patient data comprises magnetic resonance imaging (MRI) data of a tumor microenvironment within the patient and one or more metrics of the patient;

generate a patient-specific spatial model, comprising a representation of the tumor microenvironment as a three-dimensional lattice, from the MRI data within the patient data, wherein the three-dimensional lattice comprises a plurality of elastic-material points representing tissue within the tumor microenvironment;

determine a patient-specific drug interaction model based on the one or more metrics within the patient data;

determine a patient-specific metabolism model based on the one or more metrics within the patient data;

for each of one or more drug interventions, simulate the tumor microenvironment by, for each of a plurality of iterations representing time intervals, for each of the plurality of elastic-material points, modeling chemical diffusion within the tissue represented by the elastic-material point and updating one or more properties of the elastic-material point based on the modeling of chemical diffusion, wherein modeling chemical diffusion within the tissue represented by the elastic-material point comprises modeling chemical diffusion using a seven-point stencil finite difference, in which an extracellular concentration of a chemical φ at elastic-material point i is updated as:

$$\varphi_i(t + \Delta t) = \varphi_i(t) + \frac{\Delta t}{\lambda} \sum_j J_{\varphi j \to i}(t);$$

$$J_{\varphi j \to i}(t) = \frac{D_{\varphi j}(t) + D_{\varphi i}(t)}{2} \frac{\varphi_j(t) - \varphi_i(t)}{\lambda};$$

wherein λ is a lattice spacing between elastic-material points in the lattice, j indexes over six elastic-material points that neighbor elastic-material point i, $J_{\varphi j \to i}(t)$ represents a diffusive flux across a boundary separating elastic-material points j and i, $D_{\varphi i}$ is a diffusion coefficient for the chemical in elastic-material point i, and $D_{\varphi j}$ is a diffusion coefficient for the chemical in elastic-material point j, modeling one or more biochemical reactions within the tissue represented by the elastic-material point and updating one or more properties of the elastic-material point based on the modeling of the one or more biochemical reactions, modeling a metabolism of the tissue represented by the elastic-material point using the patient-specific metabolism model and updating one or more properties of the elastic-material point based on the modeling of metabolism, modeling one or more drug interactions with the tissue represented by the elastic-material point using the patient-specific drug interaction model and updating one or more properties of the elastic-material point based on the modeling of the one or more drug interactions, modeling one or both of growth and death of the tissue represented by the elastic-material point and updating one or more properties of the elastic-material point based on the modeling of one or both of growth and death, and modeling mechanical forces at the elastic-material point and updating one or more properties of the elastic-material point based on the modeling of mechanical forces; and generate and output a report for at least one of the one or more drug interventions, wherein the report comprises a graphical user interface that comprises a three-dimensional visual representation of the patient-specific spatial model after one or more of the plurality of iterations, wherein the three-dimensional visual representation indicates one or more properties of at least a subset of the plurality of elastic-material points.

\* \* \* \* \*